US010040619B2

(12) United States Patent
Py et al.

(10) Patent No.: US 10,040,619 B2
(45) Date of Patent: Aug. 7, 2018

(54) MULTIPLE DOSE DELIVERY DEVICE WITH MANUALLY DEPRESSIBLE ACTUATOR AND ONE-WAY VALVE FOR STORING AND DISPENSING SUBSTANCES, AND RELATED METHOD

(75) Inventors: Daniel Py, Larchmont, NY (US); Benoit Adamo, Pelham, NY (US)

(73) Assignee: MEDINSTILL DEVELOPMENT LLC, New Milford, CT (US)

( * ) Notice: Subject to any disclaimer, the term of this patent is extended or adjusted under 35 U.S.C. 154(b) by 0 days.

(21) Appl. No.: 13/419,352

(22) Filed: Mar. 13, 2012

(65) Prior Publication Data
US 2013/0037574 A1 Feb. 14, 2013

Related U.S. Application Data

(62) Division of application No. 11/938,144, filed on Nov. 9, 2007, now Pat. No. 8,132,695.
(Continued)

(51) Int. Cl.
*B65D 37/00* (2006.01)
*B65D 83/00* (2006.01)
(Continued)

(52) U.S. Cl.
CPC ........ *B65D 83/0033* (2013.01); *B05B 11/007* (2013.01); *B05B 11/0097* (2013.01);
(Continued)

(58) Field of Classification Search
CPC ... B05B 15/02; B05B 11/0027; B05B 11/007; B05B 11/0097; B05B 11/3032;
(Continued)

(56) References Cited

U.S. PATENT DOCUMENTS 2,252,542 A    8/1941   Beeh
2,275,595 A    3/1942   Schwartz
(Continued)

FOREIGN PATENT DOCUMENTS

DE    197 27 485 A1    1/1999
EP      0048420 A1    3/1982
(Continued)

OTHER PUBLICATIONS

International Search Report and Written Opinion of the International Searching Authority for International Application No. PCT/US2007/084356.

*Primary Examiner* — Lien Ngo
(74) *Attorney, Agent, or Firm* — McCarter & English, LLP

(57) ABSTRACT

A dispenser has a body with a variable-volume storage chamber for storing substance, and a dispensing portion defining a dosage chamber in fluid communication with the storage chamber. A first valve includes a valve seat and a flexible valve cover seated thereon defining a normally-closed fluid-tight seam therebetween. The valve cover relative to moves from the valve seat to allow substance through the seam and out of the dispenser. A second valve allows substance from the storage chamber into the dosage chamber and substantially prevents flow from the dosage chamber into the storage chamber. An actuator is manually movable between (i) a first non-actuated position, and (ii) a second actuated position extending into the dosage chamber for compressing a dose of substance therein, dispensing substance through the first valve. The elasticity of the actuator causes it to return to the first non-actuated position upon manually releasing the actuator.

20 Claims, 15 Drawing Sheets

Related U.S. Application Data

(60) Provisional application No. 60/858,155, filed on Nov. 11, 2006.

(51) Int. Cl.
  *B65D 47/18* (2006.01)
  *A61F 9/00* (2006.01)
  *B05B 11/00* (2006.01)
  *B05B 15/50* (2018.01)

(52) U.S. Cl.
  CPC .......... *B05B 11/3032* (2013.01); *B65D 47/18* (2013.01); *A61F 9/0008* (2013.01); *B05B 11/0027* (2013.01); *B05B 15/50* (2018.02)

(58) Field of Classification Search
  CPC .... B05B 15/50; B65D 83/0033; B65D 47/18; A61F 9/0008
  USPC .......... 222/207–215, 1, 321.7, 321.9, 222/384–388, 494–496, 383.1–383.3, 222/386.1, 386.5; 141/18, 20, 25–28, 59, 141/312, 314, 318, 329; 137/512, 859
  See application file for complete search history.

(56) References Cited

U.S. PATENT DOCUMENTS

| | | |
|---|---|---|
| 2,388,321 A | 11/1945 | Gereke |
| 2,442,503 A | 6/1948 | Melnikoff |
| 2,562,815 A | 7/1951 | Oscroft |
| 2,642,607 A | 6/1953 | Bozzalla |
| 2,715,236 A | 8/1955 | Tereno |
| 2,725,595 A | 12/1955 | Sisk et al. |
| 2,732,736 A | 1/1956 | Bonnie |
| 2,743,042 A | 4/1956 | Burgin |
| 3,160,329 A | 12/1964 | Radic et al. |
| 3,217,936 A | 11/1965 | Abplanalp |
| 3,220,611 A | 11/1965 | Zander et al. |
| 3,729,031 A * | 4/1973 | Baldwin .............. A61M 5/1782 141/2 |
| 3,820,689 A | 6/1974 | Cocita |
| 3,864,047 A | 2/1975 | Sherrod |
| 3,999,543 A | 12/1976 | Lacey |
| 4,002,182 A | 1/1977 | Michel |
| 4,139,311 A | 2/1979 | Lorscheidt |
| 4,301,948 A | 11/1981 | Czech et al. |
| 4,511,068 A | 4/1985 | Bossina |
| 4,564,130 A | 1/1986 | Eulenburg |
| 4,629,097 A | 12/1986 | Moore |
| 4,768,568 A | 9/1988 | Fournier et al. |
| 4,830,229 A * | 5/1989 | Ball .............................. 222/209 |
| 4,874,117 A | 10/1989 | Kay et al. |
| 4,903,868 A * | 2/1990 | Ichihara et al. .............. 222/256 |
| 4,981,479 A | 1/1991 | Py |
| 5,207,659 A | 5/1993 | Pennaneac'h et al. |
| 5,226,568 A | 7/1993 | Newton et al. |
| 5,267,673 A | 12/1993 | Crosnier et al. |
| 5,267,986 A | 12/1993 | Py |
| 5,320,845 A | 6/1994 | Py |
| 5,354,287 A | 10/1994 | Wacks |
| 5,401,259 A | 3/1995 | Py |
| 5,492,252 A | 2/1996 | Gueret |
| D368,774 S | 4/1996 | Py |
| 5,505,341 A | 4/1996 | Gueret |
| D374,719 S | 10/1996 | Py |
| 5,613,517 A | 3/1997 | Handler |
| 5,613,957 A | 3/1997 | Py |
| 5,641,004 A | 6/1997 | Morscheck |
| 5,685,869 A | 11/1997 | Py |
| 5,687,884 A | 11/1997 | Bodin et al. |
| 5,738,067 A | 4/1998 | Landwehr et al. |
| 5,746,728 A | 5/1998 | Py |
| 5,769,585 A | 6/1998 | Podolsky |
| 5,772,347 A | 6/1998 | Gueret |
| 5,816,772 A | 10/1998 | Py |
| 5,855,322 A | 1/1999 | Py |
| 5,875,931 A | 3/1999 | Py |
| 5,879,095 A | 3/1999 | Gueret |
| 5,944,702 A | 8/1999 | Py |
| 6,010,036 A | 1/2000 | Bougamont et al. |
| 6,033,384 A | 3/2000 | Py |
| 6,053,433 A | 4/2000 | Py |
| 6,073,813 A | 6/2000 | Tanner |
| RE37,047 E | 2/2001 | Py |
| 6,254,579 B1 | 7/2001 | Cogger et al. |
| 6,349,850 B1 | 2/2002 | Cheikh |
| 6,382,472 B1 | 5/2002 | Shoval |
| 6,409,406 B1 | 6/2002 | Schwartzman |
| 6,471,095 B1 | 10/2002 | Cann |
| 6,604,561 B2 * | 8/2003 | Py .................... 141/329 |
| 6,688,317 B2 | 2/2004 | Gueret |
| 6,708,846 B1 | 3/2004 | Fuchs et al. |
| 6,745,781 B2 | 6/2004 | Gueret |
| 6,752,180 B2 | 6/2004 | Delay |
| 6,761,286 B2 | 7/2004 | Py et al. |
| 6,802,601 B2 | 10/2004 | Suzuki |
| 6,892,906 B2 | 5/2005 | Py et al. |
| 7,000,806 B2 | 2/2006 | Py et al. |
| 7,226,231 B2 | 6/2007 | Py et al. |
| 7,278,553 B2 | 10/2007 | Py et al. |
| 7,322,491 B2 | 1/2008 | Py et al. |
| 7,347,389 B2 | 3/2008 | Ohnmacht et al. |
| 7,882,983 B2 * | 2/2011 | Reidt et al. .................. 222/137 |
| 8,657,481 B2 | 2/2014 | Collins |
| 2002/0017294 A1 | 2/2002 | Py |
| 2002/0023409 A1 | 2/2002 | Py |
| 2002/0074362 A1 | 6/2002 | Py et al. |
| 2003/0089743 A1 * | 5/2003 | Py .......................... A45D 40/26 222/386 |
| 2004/0112925 A1 | 6/2004 | Py et al. |
| 2004/0161292 A1 | 8/2004 | Breidenbach et al. |
| 2004/0230161 A1 | 11/2004 | Zeiner |
| 2005/0000591 A1 | 1/2005 | Py et al. |
| 2005/0016536 A1 | 1/2005 | Rapoport et al. |
| 2005/0089358 A1 | 4/2005 | Py et al. |
| 2005/0165368 A1 | 7/2005 | Py et al. |
| 2005/0194059 A1 * | 9/2005 | Py .......................... B65B 3/003 141/18 |
| 2005/0263543 A1 | 12/2005 | Py et al. |
| 2006/0065677 A1 | 3/2006 | Py et al. |
| 2006/0178642 A1 * | 8/2006 | Gillespie ............... A61M 5/001 604/228 |
| 2006/0231519 A1 | 10/2006 | Py et al. |
| 2006/0237335 A1 | 10/2006 | Py et al. |

FOREIGN PATENT DOCUMENTS

| | | |
|---|---|---|
| JP | H6-2601 Y1 | 1/1994 |
| WO | 8903363 | 4/1989 |
| WO | 03033363 A1 | 4/2003 |
| WO | WO 2004/062422 A | 7/2004 |

\* cited by examiner

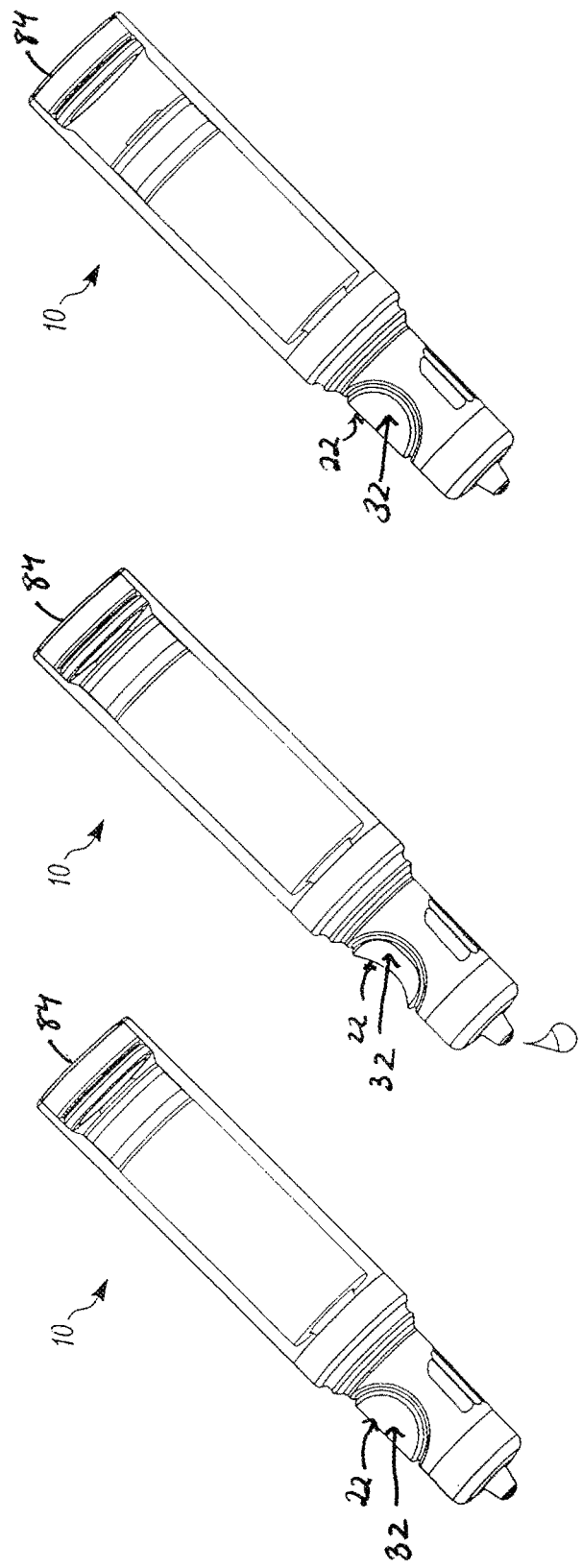

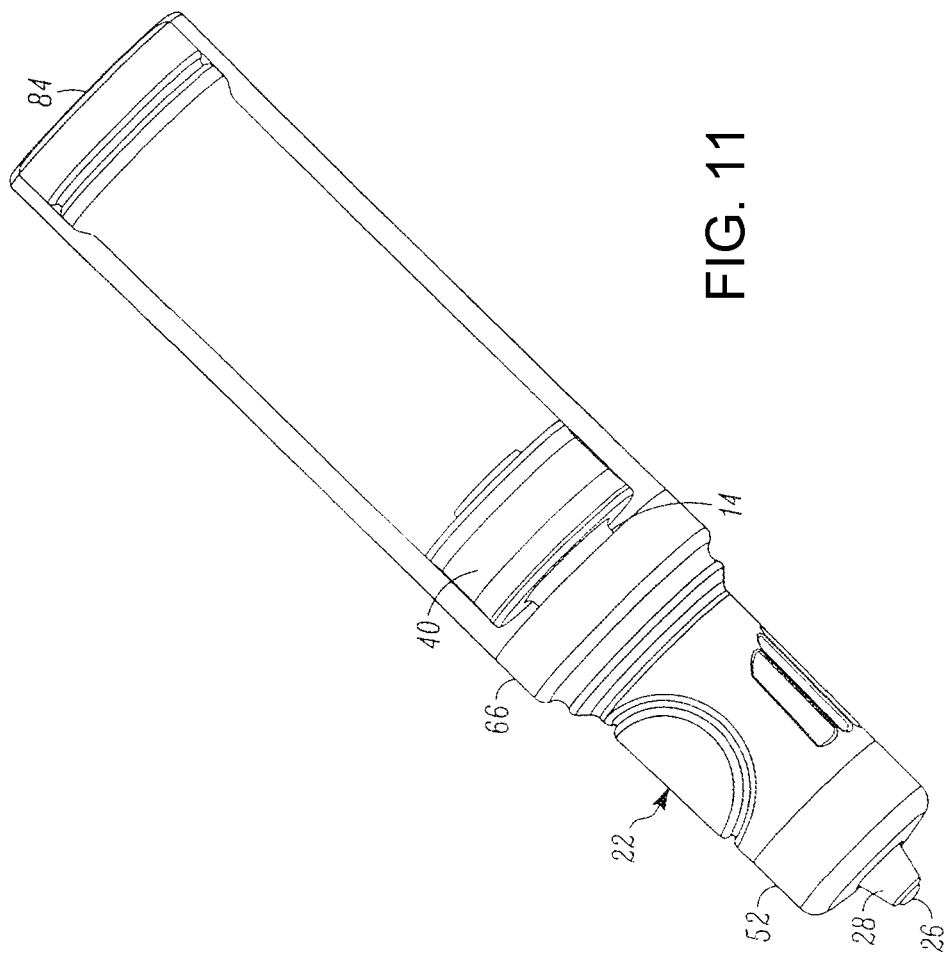

MULTIPLE DOSE DELIVERY DEVICE WITH MANUALLY DEPRESSIBLE ACTUATOR AND ONE-WAY VALVE FOR STORING AND DISPENSING SUBSTANCES, AND RELATED METHOD

CROSS-REFERENCE TO RELATED APPLICATION

This patent application is a divisional of U.S. application Ser. No. 11/938,144, filed Nov. 9, 2007, now U.S. Pat. No. 8,132,695, which claims priority to U.S. Provisional Patent Application No. 60/858,155, filed Nov. 11, 2006, which are hereby expressly incorporated by reference in their entirety as part of the present disclosure.

FIELD OF THE INVENTION

The present invention relates to dispensers for containing and dispensing fluids and other substances, such as pharmaceutical, cosmeceutical, cosmetic, food and beverage products, and more particularly, to dispensers for holding multiple doses of such fluids and other substances, and that include one-way valves for hermetically sealing the substances within the dispensers, and manually engageable actuators for dispensing doses of substances through the one-way valves.

BACKGROUND INFORMATION

Prior art dispensers for storing and dispensing multiple doses of substances, such as cosmetic dispensers for dispensing, for example, liquid lipstick or eye shadow, ophthalmic dispensers for dispensing ophthalmic products, such as eye drops, pharmaceutical dispensers for dispensing pharmaceutical products, food and beverage dispensers for dispensing food or beverage products, typically do not store the product, which may take the form of a liquid, cream, gel, suspension or other format, in a hermetically sealed storage chamber. In addition, such dispensers may be exposed to, and/or are applied to a user's facial or other body surfaces, or to other elements, that may contain dirt, germs, bacteria or other unwanted contaminants. Such contaminants can penetrate through the dispensing openings in the dispensers and, in turn, contaminate the bulk of the products stored within the dispensers. As a result, the contaminants can be passed from one user to another or otherwise cause unhealthy conditions with further usage of the dispensers. Further, because the products stored within the dispensers are exposed to air, the products can degrade or spoil, and/or require preservatives to prevent such degradation and/or spoilage from occurring. In some circumstances, preservatives can cause allergic and/or other undesirable or negative reactions, such as unwanted dermatological reactions, or irritation of the eyes, skin or other tissues.

In some dispensers including storage chambers for storing multiple doses of substances, the storage chambers can define a smaller volume than otherwise desired. In addition, it can be difficult to increase the volume of the storage chamber if desired. In other dispensers with pumps or other mechanisms for propelling a dose from the dispenser, the dose can spritz when emitted from the dispenser, and this can be undesirable when used, for example, for ophthalmic delivery.

It is an object of the present invention to overcome one or more of the above-described drawbacks and/or disadvantages of the prior art.

SUMMARY OF THE INVENTION

In accordance with one aspect, the present invention is directed to a dispenser for dispensing a substance, comprising a body defining a variable-volume storage chamber for storing the substance. A dispensing portion is connected with the body and defines a dosage chamber coupled in fluid communication with the storage chamber for receiving substance therefrom, and an outlet aperture coupled in fluid communication with the dosage chamber. A first valve includes an axially-extending valve seat and an axially-extending flexible valve cover seated on the valve seat and defining a normally-closed, axially-extending seam therebetween forming a fluid-tight seal between the valve cover and valve seat. The flexible valve cover is movable relative to the valve seat and the seam is connectable in fluid communication with the outlet aperture to allow the passage of substance through the seam and out of the dispenser. A second valve is coupled in fluid communication between the dosage chamber and the storage chamber that allows the flow of substance from the storage chamber into the dosage chamber and substantially prevents the flow of substance from the dosage chamber into the storage chamber. An elastic actuator, such as a manually-engageable actuator, is mounted on the dispensing portion and is movable between (i) a first non-actuated position, and (ii) a second actuated position for compressing a dose of substance within the dosage chamber and, in turn, dispensing the substance through the first valve. The elasticity of the actuator causes the actuator to return from the second actuated position to the first non-actuated position upon releasing the actuator.

In one embodiment of the present invention, the second valve is a check valve. In one such embodiment, the check valve is a flap valve.

In one embodiment of the present invention, the dispensing portion includes a dispensing body defining the dosage chamber, outlet aperture and valve seat, and the elastic actuator is co-molded to the dispensing body.

In one embodiment of the present invention, the elastic actuator is in fluid communication with the dosage chamber, and extends into the dosage chamber in the second actuated position. In one such embodiment, the actuator extends axially in a direction approximately parallel to an axis of symmetry of the dispenser, and extends angularly about the axis of symmetry. In one such embodiment, the actuator extends angularly through an arc within the range of about 50° to about 80°. In one such embodiment, a manually-engageable surface of the actuator is located a substantially uniform distance from the axis of symmetry in the non-actuated position.

In one embodiment of the present invention, the body forming the storage chamber includes a flexible tube. In one such embodiment, the body further includes a tube head connected to the flexible tube. In one such embodiment, the tube head is co-molded, such as by insert molding, with the flexible tube.

In one embodiment of the present invention, the flexible valve cover is responsive to a flow of substance in the outlet aperture exceeding a valve opening pressure to move between (i) a normally-closed condition, and (ii) an open condition wherein portions of the valve cover axially spaced relative to each other substantially sequentially move substantially radially relative to the valve seat to allow the passage of substance through the seam and out of the dispenser.

One embodiment of the present invention further comprises a stopper slidably received within the body and forming a substantially fluid-tight seal therebetween. The variable-volume storage chamber is formed between the stopper and the dosage chamber, and the stopper is movable toward the dosage chamber upon dispensing a dose from the storage chamber to reduce the volume of the storage chamber in an amount approximately equal to the volume of the dose dispensed. One such embodiment further comprises a flexible membrane coupled between the stopper and an end portion of the body opposite the dispensing portion, and forming a substantially fluid-tight seal between the annular stopper and respective end portion of the body. In one such embodiment, the flexible membrane includes a plurality of laminated layers. In one such embodiment, the flexible membrane extends annularly about the stopper and about the respective end portion of the body. In one embodiment of the present invention, the stopper includes a needle penetrable and thermally resealable portion.

In accordance with another aspect, the stopper includes at least one relatively rigid annular sealing portion forming an interference fit with the body, and at least one relatively flexible annular sealing portion forming an interference fit with the body and a fluid-tight seal therebetween. In one such embodiment, the relatively rigid and relatively flexible portions are co-molded. In some such embodiments, the relatively flexible portion further defines a penetrable and thermally resealable portion that is penetrable by a filling member to fill the variable-volume storage chamber and is thermally resealable to thermally reseal an aperture therein. In one such embodiment, the flexible sealing portion is substantially concentric with the penetrable portion, and a gap is formed therebetween.

In one embodiment of the present invention, at least one of the valve cover and the valve seat defines at the seam at least one relatively raised surface area and at least one adjacent relatively recessed surface area to prevent spritzing of a dose of the substance upon emission from the valve. In one such embodiment, at least one of the valve cover and the valve seat defines a plurality of relatively raised surface areas and relatively recessed surface areas adjacent to relatively raised surface areas. In one such embodiment, the valve cover includes a first portion defining a first degree of radial interference with the valve seat in the normally closed position, and a second portion axially spaced relative to the first portion defining a second degree of radial interference with the valve seat in the normally closed position. In one such embodiment, the second degree of radial interference is less than the first degree of radial interference. In one such embodiment, the second degree of radial interference is approximately zero or less. Also in one such embodiment, the second portion is located outwardly on the first valve relative to the first portion.

In one embodiment of the present invention, the valve cover extends annularly about the valve seat, and the dispenser further comprises a securing member fixedly connected to the dispensing portion and compressing a portion of the valve cover therebetween to, in turn, form a fluid tight seal between the valve cover and the dispensing portion. The securing member extends annularly about the valve cover, and extends axially along a substantial portion of the valve cover. In one such embodiment, a distal portion of the valve cover extends outwardly of the securing member.

In accordance with another aspect, the present invention is directed to a dispenser for dispensing a substance, comprising:

first means for forming a variable-volume storage chamber for storing the substance;

second means for forming a dosage chamber coupled in fluid communication with the storage chamber for receiving substance therefrom, and an outlet aperture coupled in fluid communication with the dosage chamber;

third means for forming a normally-closed, axially-extending seam coupled in fluid communication with the second means and movable in response to the flow of pressurized substance from the second means into the seam to allow the passage of substance through the seam and out of the dispenser;

fourth means coupled in fluid communication between the dosage chamber and the storage chamber for allowing the flow of substance from the storage chamber into the dosage chamber and substantially preventing the flow of substance from the dosage chamber into the storage chamber; and fifth means for engaging and elastically moving between (i) a first non-actuated position, and (ii) a second actuated position for compressing a dose of substance within the dosage chamber and, in turn, dispensing the substance through the third means, and for elastically returning from the second actuated position to the first non-actuated position upon releasing the fifth means.

In one embodiment of the present invention, the first means is a body portion of the dispenser; the second means is a dispensing portion connected with the body and defining a dosage chamber coupled in fluid communication with the storage chamber for receiving substance therefrom, and an outlet aperture coupled in fluid communication with the dosage chamber; the third means is a first valve including an axially-extending valve seat and an axially-extending flexible valve cover seated on the valve seat and defining a normally-closed, axially-extending seam therebetween forming a fluid-tight seal between the valve cover and valve seat, wherein the flexible valve cover is movable relative to the valve seat and the seam is connectable in fluid communication with the outlet aperture to allow the passage of substance through the seam and out of the dispenser; the fourth means is a second valve coupled in fluid communication between the dosage chamber and the storage chamber that allows the flow of substance from the storage chamber into the dosage chamber and substantially prevents the flow of substance from the dosage chamber into the storage chamber; and the fifth means is an elastic actuator mounted on the dispensing portion in fluid communication with the dosage chamber and movable between (i) a first non-actuated position, and (ii) a second actuated position for compressing a dose of substance within the dosage chamber and, in turn, dispensing the substance through the first valve.

In one embodiment of the present invention, the dispenser further comprises sixth means for substantially preventing the substance from spritzing upon being dispensed from the third means. In one such embodiment, the sixth means is defined by at least one of a valve cover and a valve seat defining at a seam formed therebetween at least one relatively raised surface area and at least one adjacent relatively recessed surface area.

In accordance with another aspect, the present invention is directed to a method comprising the following steps:

providing a sealed, empty device including a body, a slidable stopper received within the body and defining a variable-volume storage chamber therein, a one-way valve, a dosage chamber connectable in fluid communication between the one-way valve and variable-volume storage chamber, and an actuator movable between a non-actuated position and an actuated position for compressing a dose of fluid within the dosage chamber and dispensing the dose through the one-way valve;

penetrating the stopper with a filling member and the stopper located in a first position within the body;

moving the filling member and stopper to a second position with the body;

filling the variable-volume storage chamber with a fluid through the filling member;

moving the filling member and stopper from the second position back to the first position while filling the variable-volume storage chamber;

withdrawing the filling member; and thermally sealing an aperture in the stopper to seal the filled variable-volume storage chamber.

In some embodiments, the method further comprises the step of sterilizing the sealed empty device prior to filling. Some embodiments further comprise the step of drawing a vacuum through at least one of the needle and a filling aperture during the filling step. Some embodiments further comprise drawing with the vacuum source filled fluid out of the variable-volume storage chamber and into a filling member conduit and/or a collection container coupled in fluid communication with the filling member upon filling the chamber, and withdrawing the filling member to thereby leave substantially zero air within the chamber. Some embodiments further comprise the step of providing an overpressure of sterile air over at least one of the filling member and device during filling.

One advantage of currently preferred embodiments of the present invention is that the storage chamber may be defined by a flexible tube, or a rigid body with a sliding stopper or piston received within the rigid body. In the flexible tube embodiments, the tubes can take any of numerous different shapes or sizes, and the same or substantially the same type of dispensing portion can be connected to different sized tubes. As a result, the dispenser can provide significant flexibility with respect to storing and dispensing various desired volumes of substances. Another advantage of certain preferred embodiments of the present invention, is that the dispenser can deliver substantially one drop of substance at a time, and the drop can be delivered substantially without spritzing. This can be particularly advantageous in the ophthalmic applications of the dispenser. Yet another advantage of currently preferred embodiments of the present invention is that substantially predetermined volumes of substances can be delivered with each dose. A still further advantage of currently preferred embodiments of the present invention is that the substance can be retained within the storage chamber in a sterile, substantially airless, hermetically sealed condition during both the shelf life, and during the period of use of the dispenser (i.e., throughout the period from dispensing the first to the last dose of substance from the storage chamber). Another advantage of such embodiments is that the substance may be preservative free.

Other objects and advantages of the present invention, and/or of the currently preferred embodiments thereof, will become apparent in view of the following detailed description of the currently preferred embodiments and the accompanying drawings.

BRIEF DESCRIPTION OF THE DRAWINGS

FIGS. 10A-10F are a series of side elevational views of the dispenser of FIG. 1 illustrating the body as transparent and the manner in which the manually-engageable, elastic actuator is manually depressed to dispense a drop of substance, how the sliding piston correspondingly moves forward to reduce the volume of the storage chamber in an amount approximately equal to the volume of the drop dispensed, and how the process is repeated for the delivery of subsequent doses.

FIG. 11 shows the dispenser of FIG. 1 in an empty condition.

DETAILED DESCRIPTION OF THE INVENTION

Figure 1:
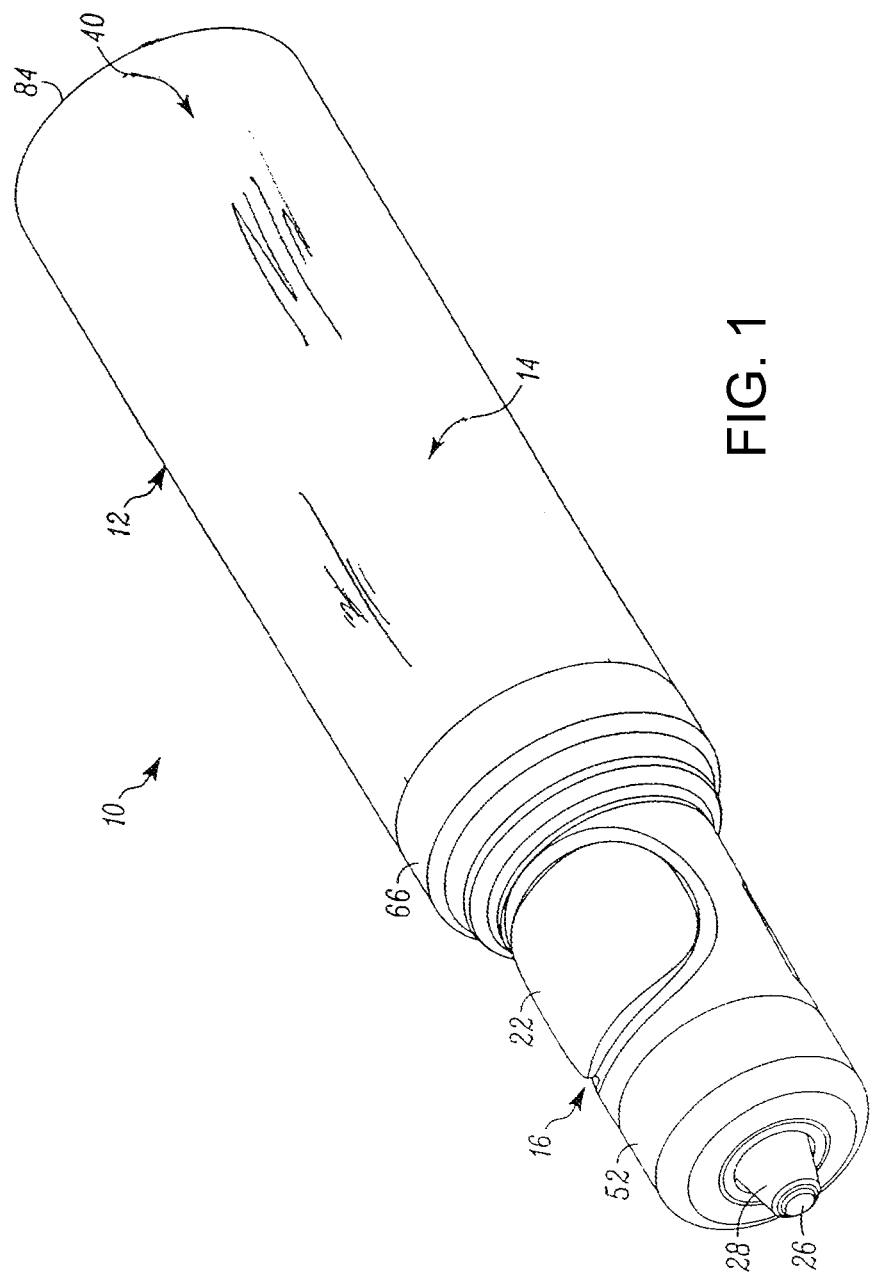
FIG. 1 is an upper perspective view of a first embodiment of a dispenser of the present invention.

Referring to FIGS. 1-11, a dispenser embodying the present invention is indicated generally by the reference numeral 10. The dispenser 10 is particularly suitable for dispensing fluids and other substances, such as pharmaceutical, cosmeceutical, cosmetic, ophthalmic, food and beverage products. However, as may be recognized by those of ordinary skill in the pertinent art based on the teachings herein, the dispenser 10 may be adapted to dispense any of numerous different types of fluids or other substances that are currently known, or that later become known. As shown typically in FIG. 1, the dispenser 10 includes a body 12 defining a variable-volume storage chamber 14 for storing the substance, such as a pharmaceutical, cosmeceutical, cosmetic, ophthalmic, food or beverage product. A dispensing nozzle or portion 16 is connected with the body 12 and defines a dosage chamber 18 coupled in fluid communication with the storage chamber 14 for receiving the stored substance therefrom, and at least one outlet aperture 20 coupled in fluid communication with the dosage chamber 18. An elastic actuator 22 is receivable within the dosage chamber 18, and a dispensing nozzle or one-way valve 24 is mounted on the dispensing portion 16 for dispensing the stored substance therethrough.

The dispensers disclosed herein are similar to those disclosed in U.S. patent application Ser. No. 11/237,599, entitled "Laterally-Actuated Dispenser with One-Way Valve for Storing and Dispensing Metered Amounts of Substances", like titled U.S. Provisional Application No. 60/613,583, filed Sep. 27, 2004, and U.S. Provisional Application No. 60/699,607 filed Jul. 15, 2005, and U.S. Design patent application No. 29/214,062, filed on Sep. 27, 2004 entitled "Dispenser with Laterally-Actuated Dispensing Valve", each of which is hereby incorporated by reference in its entirety as part of the present disclosure.

As shown in FIGS. 2-6, the one-way valve 24 includes an axially-extending valve seat 26, and an axially-extending flexible valve cover 28 seated on the valve seat and defining a normally-closed, axially-extending seam 30 therebetween forming a fluid-tight seal between the valve cover 28 and valve seat 26. As described further below, the flexible valve cover 28 is movable relative to the valve seat 26, and the seam 30 is connectable in fluid communication with the outlet aperture 20 to allow the passage of product through the seam and out of the dispenser.

Figure 2:
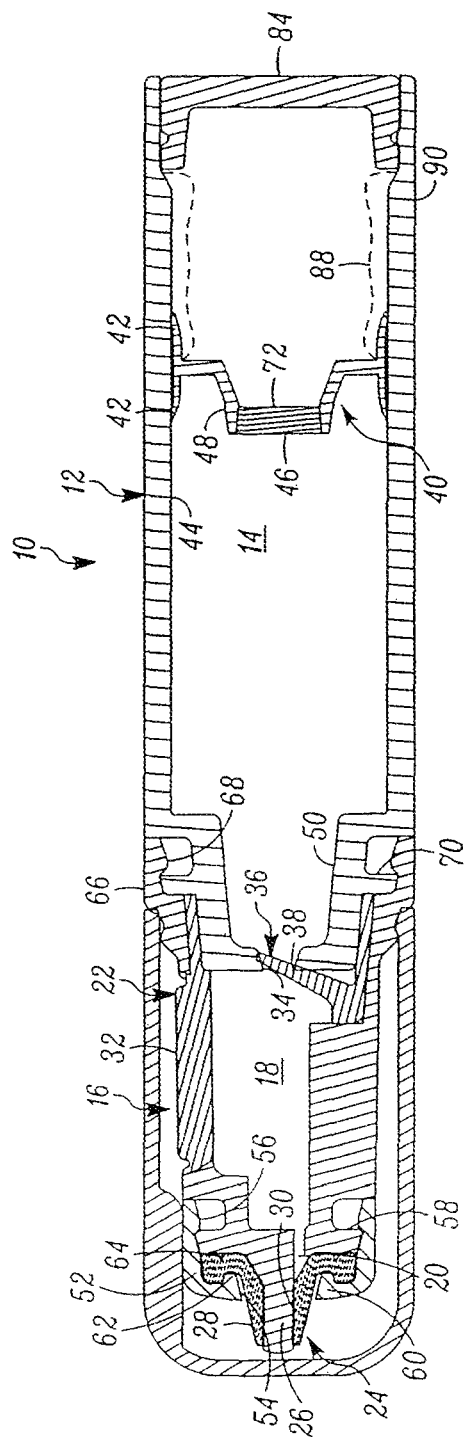
FIG. 2 is a cross-sectional view of the dispenser of FIG. 1.
Figure 9:
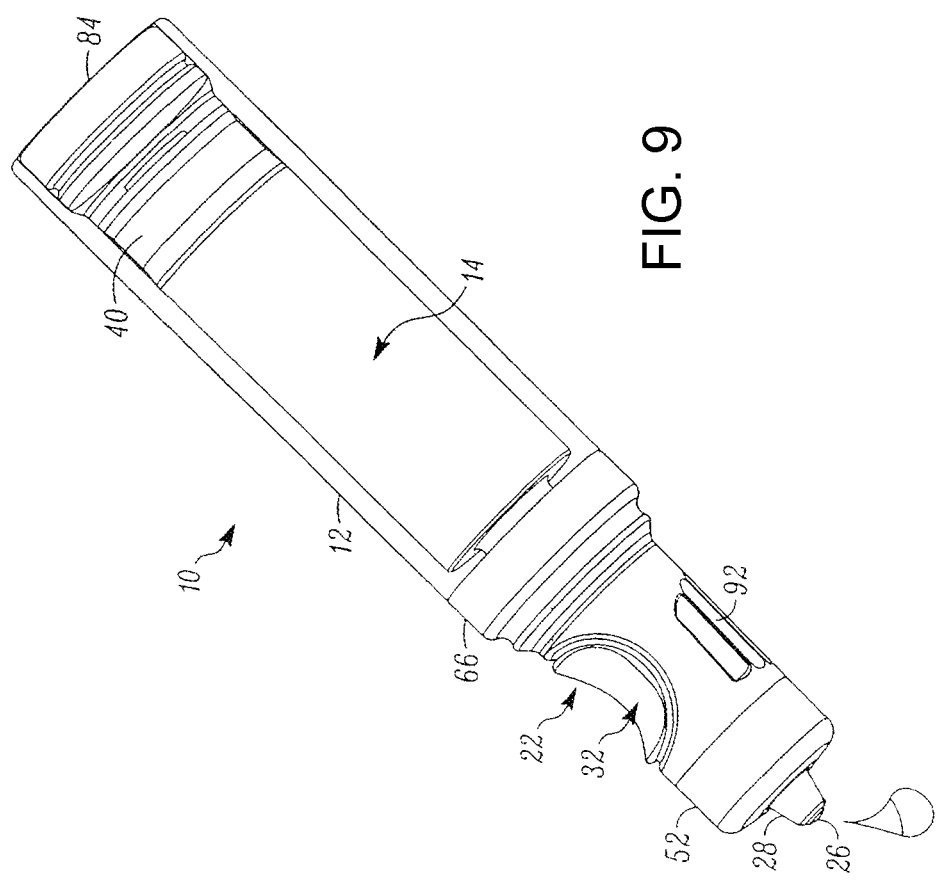
FIG. 9 is a side elevational view of the dispenser of FIG. 1 illustrating the body as transparent to show exemplary features within it, the manually-engageable, elastic actuator in the second actuated position, and a resulting drop of substance released from the dispensing tip of the one-way valve.

The actuator 22 is a manually-engageable, elastic actuator that is mounted on the dispensing portion 16 and is manually movable between (i) a first non-actuated position, as shown typically in FIGS. 1 and 2, and (ii) a second actuated position, as shown typically in FIG. 9, for compressing a dose of substance within the dosage chamber 18 and, in turn, dispensing the substance through the one-way valve 24. As described further below, the elasticity of the actuator 22 causes the actuator to return from the second actuated position (FIG. 9) to the first non-actuated position (FIG. 1) upon releasing the actuator. As can be seen, the actuator 22 is laterally positioned with respect to the one-way valve 24, is in fluid communication with the dosage chamber 18, extends axially in a direction approximately parallel to an axis of symmetry of the dispenser 10, extends angularly about the axis of symmetry, and in the second actuated position (FIG. 9) extends into the dosage chamber 18. In one embodiment of the present invention, the elastic actuator 22 extends angularly through an arc within the range of about 50° to about 80°. As also shown in the illustrated embodiment, the manually-engageable surface 32 of the actuator 22 is located a substantially uniform distance from the axis of symmetry in the non-actuated position (FIG. 2). The actuator 22 defines a drive axis or direction extending between the non-actuated or rest position of FIG. 1 and the actuated position of FIG. 9, and the drive axis is oriented transverse to the axis of the one-way valve 24 and body 12. In the illustrated embodiment of the present invention, the drive axis of the actuator is oriented at about 90° relative to the axis of the one-way valve and body. However, the drive axis may be oriented at any of numerous angular orientations in order to facilitate the manufacture of the dispenser, to facilitate manipulation or actuation of the dispenser, or otherwise to improve the ergonomics of the dispenser.

As indicated above, the one-way valve 24 includes a relatively rigid valve seat 26 and a flexible valve cover 28 mounted over the valve seat and defining the axially elongated, annular seam or interface 30 therebetween. As described further below, the actuator 22 forces a dose of fluid or other substance at sufficient pressure to open the valve (the "valve opening pressure") and force the fluid or other substance through the valve interface 30 and out of the dispenser. The valve cover 28 preferably forms an interference fit with the valve seat 26 to thereby form a fluid-tight seal in the normally closed position and, in turn, maintain the fluid or other substance within the dispenser in a sterile and hermetically sealed condition. As shown typically in FIGS. 1 and 2, the valve cover 28 may define a substantially tapered cross-sectional shape moving in the axial direction from the interior toward the exterior of the valve. This configuration requires progressively less energy to open each respective annular portion of the valve when moving axially from the interior toward the exterior of the valve. Alternatively, or in combination with the tapered valve cover 28, the valve seat 26 may define an outer diameter that progressively or otherwise increases in the axial direction toward the valve tip, to provide the same or similar effect. As a result, once the base of the valve 24 is opened, the pressure is sufficient to cause the respective axial segments of the valve cover 28 to progressively open and then close after passage of substance therethrough when moving in the axial direction toward the valve tip to dispense a dose. Also, at any time when dispensing a dose, preferably any one of a plurality of different substantially annular segments of the valve cover 28 engages the valve seat 26 to maintain a fluid-tight seal across the valve 24, and thereby prevent ingress through the valve of germs, bacteria or other unwanted substances and into the storage chamber 14. The volume of the dose may be varied depending upon the degree to which the actuator 22 is depressed when moved from the first non-actuated position (FIG. 2) to the second actuated position (FIG. 9).

In the illustrated embodiment the dispensing portion 16 includes a single outlet aperture 20 for each dose. If desired, additional outlet apertures may be added (e.g., a second outlet aperture of the same or different size diametrically opposed to the illustrated aperture 20, or a different plurality of substantially equally spaced apertures may be provided), or the aperture 20 may be moved to a position other than that shown (e.g., the single outlet aperture may be located on the opposite side of the valve seat relative to that shown).

The valve seat 26 and dosage chamber 18 are formed integral with each other on the dispensing portion 16 and are formed of a relatively rigid material. A fluid passageway 34 extends between the storage chamber 14 and the dosage chamber 18 for permitting the flow of fluid or other substance from the storage chamber 14 into the dosage chamber 18.

A check valve or anti-reflux valve 36 is mounted on the downstream side of the fluid passageway 34 to prevent substance within the compression chamber 18 from flowing back into the variable-volume storage chamber 14 after depressing the actuator 22. In the illustrated embodiment, the check valve 36 is formed integral with the actuator 22, and is defined by a laterally extending lobe or flap 38 that overlies the downstream side (i.e., the dosage chamber 18 side) of the fluid passageway 34 to normally close the passageway. As can be seen, as the actuator 22 is manually depressed, the flap 38 of the check valve 36 is forced against the downstream side of the fluid passageway 34 to seal the opening to the passageway and, in turn, seal the compression chamber 18 with respect to the variable-volume storage chamber 14, and thereby prevent any substance from flowing in the direction from the compression chamber 18 back into the variable-volume storage chamber 14 during the compression stroke of the actuator. When the user releases the actuator 22, the inherent elasticity of the actuator 22 drives the actuator back into the ambient or rest position, as shown typically in FIG. 2. Upon movement of the actuator 22 from the actuated position (FIG. 9) to the rest or ambient position (FIG. 2), the substance in the variable-volume storage chamber 14 is drawn through the fluid passageway 34, over the flap 38 of the check valve 36, and into the dosage chamber 18 to fill the dosage chamber for the next dose.

In the illustrated embodiments, the body of the dispensing portion 16 is made of a relatively hard plastic material, such as any of the plastics sold under the trademarks Topaz™, Surlyn™, and Zeonex™. The valve cover 28 and elastic actuator 22, on the other hand, are each made of an elastic or elastomeric material that is relatively soft in comparison to the body and valve seat 26. For example, the valve cover 28 and actuator 22 each may be made of a polymeric material, such as one of the materials sold under the trademarks Kraton™ or Santoprene™ (e.g., Santoprene 8211-35 (shore 35 hardness) or 8211-55 (shore 55 hardness)), Rimflex™, such as Rimflex A/AS 25C, Dynaflex G2706, or a vulcanized rubber or other polymeric material. The actuator 22 is formed of a material that defines a radial thickness and durometer such that the actuator has sufficient elasticity to return itself from the second actuated position (FIG. 9) to the first non-actuated position (FIG. 2) upon release. In one embodiment of the present invention, the actuator 22 defines a thickness within the range of about 1 to 3 mm, and preferably within the range of about 1.5 to about 2 mm, and a durometer within the range of about 20 to about 40 shore A, and preferably within the range of about 25 to about 35 shore A. Also in the illustrated embodiment, the actuator 22 and check valve 36 are co-molded with the body of the dispensing portion 12, such as by over-molding the actuator and check valve to the body. However, as may be recognized by those of ordinary skill in the pertinent art based on the teachings herein, these materials and methods of manufacture are only exemplary, and numerous other materials and methods of manufacture that are currently known, or that later become known equally may be used.

The dispenser 10 further includes a plunger 40 (also referred to as a sliding piston or stopper) that is slidably received within the body 12 and axially spaced relative to the actuator 22 and dosage chamber 18 to define the variable-volume storage chamber 14 therebetween. The plunger 40 includes at least one, and preferably two axially spaced, outer annular sealing members or portions 42 that sealingly engage the inner wall 44 of the body 12 to form a fluid-tight seal therebetween. The sealing members or portions 42 may be formed integral with the plunger 40, such as by forming thereon annular protuberances, as shown, that form a radial interference fit with the inner wall 44, or may be formed by sealing members, such as o-rings or other sealing members, that are received within corresponding grooves or recesses formed in the plunger. As the actuator 22 is progressively actuated, the plunger 40 slides forwardly within the dispenser body 12 (or in the direction of right to left in FIG. 2) due to the suction forces exerted thereon as the fluid or other stored substance is dispensed from the variable-volume storage chamber 14.

The plunger 40 defines a substantially flat inner surface 46, and a substantially conical tapered portion 48 extending between the inner surface 46 and the annular sealing surfaces 42. As can be seen, the inner end of the body 12 defines a substantially conically-tapered recess 50 for receiving therein the plunger 40. When the variable-volume storage chamber 14 is substantially emptied of the substance stored therein, the flat surface 46 and conically-tapered portion 48 of the plunger 40 are received within the recess 50 of the body 12. One advantage of this configuration is that it substantially eliminates any dead volume in the dispenser when emptied and thus any waste of product stored therein.

The dispenser 10 further comprises an approximately annular securing member 52 coupled to the dispensing portion 16 and fixedly securing the valve cover 28 thereto. The securing member 52 defines an aperture 54 extending through a central portion thereof for receiving the dispensing tip of the one-way valve 24 therethrough, an annular, laterally-extending flange 56 formed on the inner end thereof and received within a corresponding annular groove 58 formed on the dispensing portion 16 for fixedly securing the securing member 52 and thus the valve cover 28 to the dispensing portion 16, and an annular, axially-extending flange 60 formed on the inner periphery of the aperture 54 that is received within a corresponding annular groove 62 formed on the valve cover 28 to compress the valve cover against the dispensing portion and form a fluid-tight seal therebetween. The dispensing portion includes an annular spike 64 that is pressed into engagement with the compressed portion of the valve cover 28 to further effect a fluid-tight seal between the valve cover and securing member 52. The dispensing portion 16 further includes on the end opposite the one-way valve 24 a connecting portion 66 including an annular, laterally-extending flange 68 that is received within a corresponding annular groove 70 formed on the body 12 to fixedly secure the dispensing portion 16 to the body 12.

Figure 3:
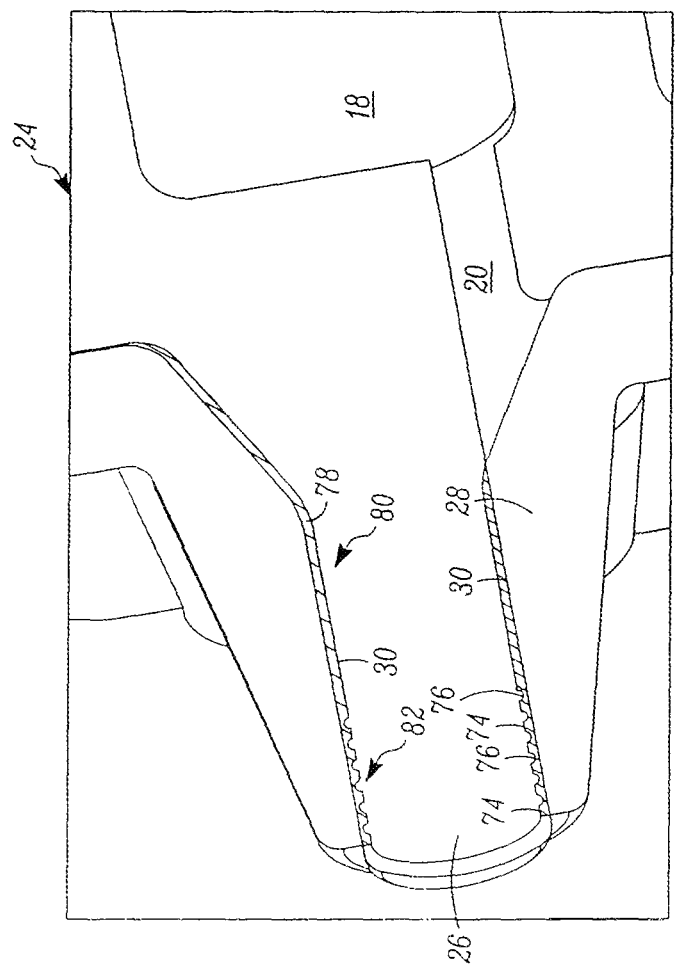
FIG. 3 is a partial, enlarged, cross-sectional view of the one-way valve of the dispenser of FIG. 1.
Figure 4:
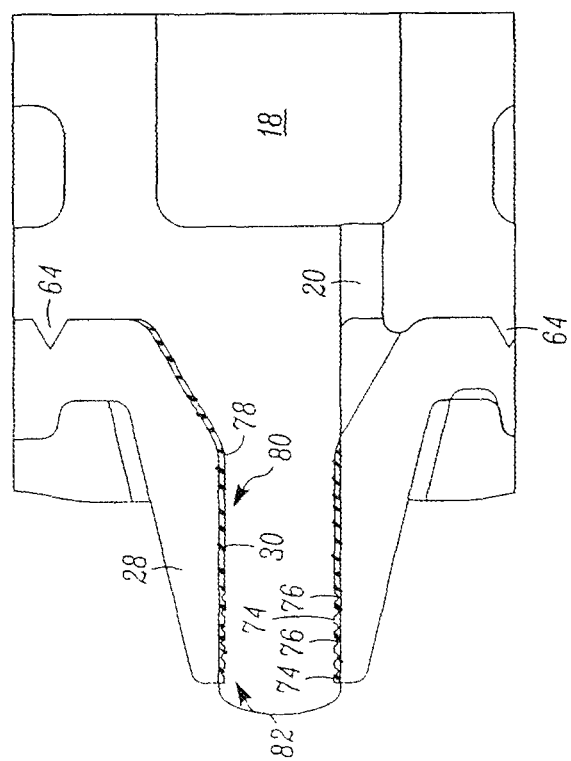
FIG. 4 is another partial, enlarged, cross-sectional view of the one-way valve of the dispenser of FIG. 1.
Figure 5:
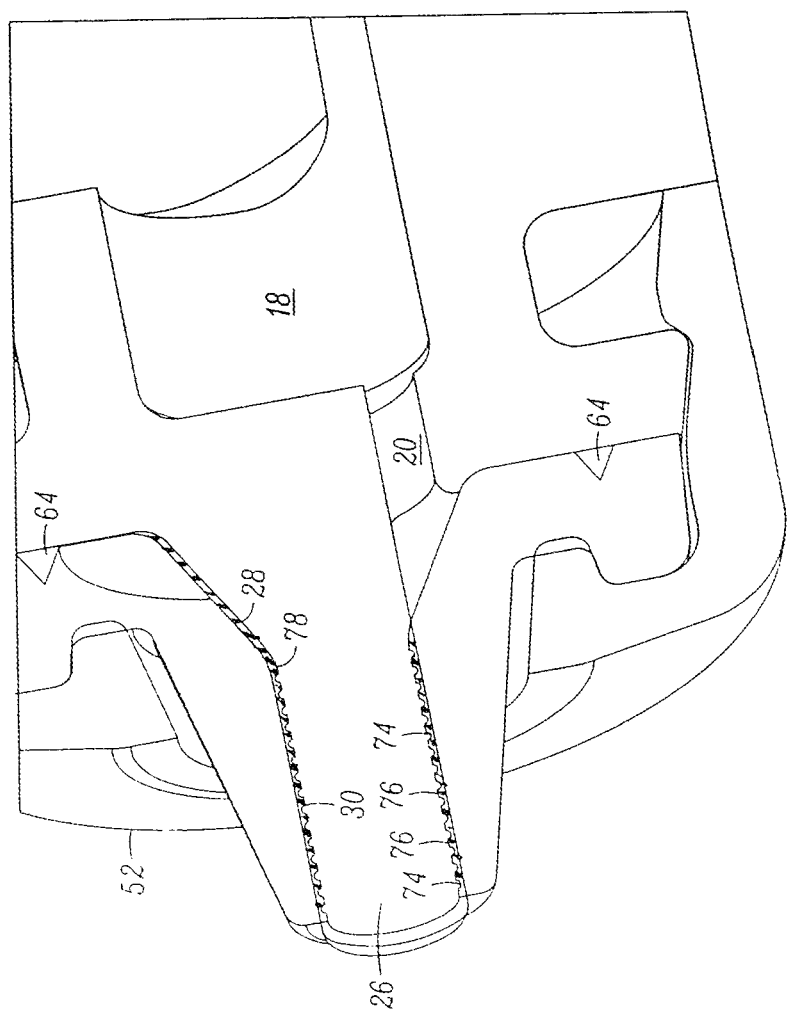
FIG. 5 is a partial, enlarged, perspective cross-sectional view of another embodiment of the one-way valve of the dispenser of FIG. 1.
Figure 6:
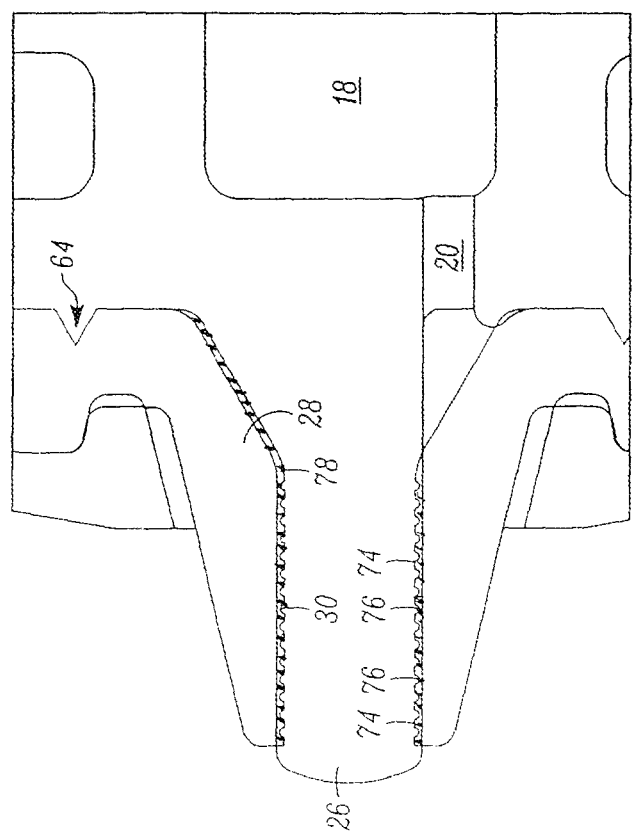
FIG. 6 is another partial, enlarged, cross-sectional view of the embodiment of the one-way valve of FIG. 5.

The one-way valve 24 preferably further includes means for substantially preventing the substance from spritzing upon being dispensed (or upon emission) from the one-way valve 24. In the illustrated embodiments, such means takes the form of at least one of the valve cover 28 and the valve seat 26 defining at the seam 30 formed therebetween at least one relatively raised surface area 74 and at least one adjacent relatively recessed surface area 76. In the embodiment of FIGS. 3 and 4, the valve cover 28 defines plurality of relatively raised surface areas 74 that are axially spaced relative to each other, and a plurality of relatively recessed surface areas 76 formed therebetween. Also in the illustrated embodiment, the relatively raised surface areas 74 are defined by annular rings, and the relatively recessed surface areas 76 are defined by corresponding annular grooves. As shown in FIGS. 3 and 4, the one-way valve 24 defines an axially-extending region 78 of radial interference at the seam 30 between the valve cover 28 and valve seat 26 to effect the fluid-tight seal therebetween in the normally closed position. In the illustrated embodiment, the valve cover 28 and valve seat 26 define a first axially-extending portion 80 forming a first degree of radial interference in the normally closed position, and a second axially-extending portion 82 axially spaced relative to the first portion 80 forming a second degree of radial interference in the normally closed position. In the embodiment of FIGS. 3 and 4, the second degree of radial interference at the second portion 82 is less than the first degree of radial interference at the first portion 80. In FIGS. 3 and 4 the degree of radial interference is approximately indicated graphically by the thickness of the cross-hatching defining the radial interference region 78 in the respective portion. As can be seen, the radial interference in the second portion 82, and particularly in the annular regions of the second portion defined by the relatively raised surface areas 74, is significantly less than in the first portion 80. In one such embodiment, the second degree of radial interference at least at the relatively raised surface areas 74 is approximately zero or less. As can be seen in the illustrated embodiment, the second portion 82 defining the lesser degree of radial interference 78 is located outwardly on the one-way valve 24 relative to the first portion 80. When a dose of substance is dispensed through the seam 30 of the one-way valve 24, the valve cover 28 may initially stick to the valve seat 26, thus creating a build-up of pressure within the valve. The second region 82 of the seam absorbs and/or dissipates the energy resulting from any such pressure build-up, and in turn substantially prevents the dose from spritzing upon emission from the valve. In ophthalmic applications, the dose is preferably delivered as a drop that falls from the dispensing tip into a user's eye. As shown, the valve cover 28 defines a relatively raised portion 74 rather than a recessed portion 76 at the distal end of the valve cover 28 to ensure formation of a seal at this region and thus substantially prevent the collection of residue that otherwise might become contaminated between usages.

As may be recognized by those of ordinary skill in the pertinent art based on the teachings herein the anti-spritzing feature may take any of numerous different configurations that are currently known, or that later become known for performing this function. For example, as shown in the alternative embodiment of FIGS. 5 and 6, the relatively raised portions 74 and adjacent relatively recessed portions are formed on the valve seat 26 rather than on the valve cover 28. Also in this embodiment, the relatively raised and recessed surface portions 74, 76 extending axially throughout substantially the entire seam 30 of the one-way valve 24. The degree of radial interference may be the same for the relatively raised surface areas, and for the relatively recessed surface areas, but greater for the recessed surface areas 76 then for the raised surface areas 74. However, the degree of radial interference may be varied as desired or otherwise required to achieve the anti-spritzing objective. In addition, as may be recognized by those of ordinary skill in the pertinent art based on the teachings herein, the surface features may take any of numerous different configurations that are currently known, or that later become known for purposes of achieving the anti-spritzing function, while nevertheless maintaining a fluid-tight seal in the normally-closed position.

In a currently preferred embodiment of the present invention, the plunger 40 includes a needle penetrable and resealable stopper or like portion 72 that permits the variable-volume storage chamber 14 to be needle filled with a substance therethrough, and that allows the resulting needle hole to be thermally resealed, such as by application of laser energy thereto. In the illustrated embodiment, the stopper 72 is co-molded with the body of the plunger, such as by over-molding the stopper to the body. The needle penetrable and resealable portion of the plunger or resealable stopper or like portion 72 thereof (or other desired needle penetrable and thermally resealable portion of the dispenser), may be formed with any of the various materials disclosed in, and may be needle filled and resealed in accordance with the various teachings of, the following patents and co-pending patent applications that are assigned to the Assignee of the present invention and are hereby expressly incorporated by reference in their entireties as part of the present disclosure: U.S. Pat. No. 6,604,561, entitled "Medicament Vial Having a Heat-Sealable Cap, and Apparatus and Method for Filling the Vial"; U.S. Pat. No. 6,684,916, entitled "Medicament Vial Having a Heat-Sealable Cap, and Apparatus and Method for Filling the Vial"; U.S. Pat. No. 6,805,170, entitled "Medicament Vial Having a Heat-Sealable Cap, and Apparatus and Method for Filling the Vial"; U.S. Pat. No. 7,243,689, entitled "Medicament Vial Having a Heat-Sealable Cap, and Apparatus and Method for Filling the Vial"; U.S. Pat. No. 7,032,631, entitled "Medicament Vial Having a Heat-Sealable Cap, and Apparatus and Method for Filling the Vial"; U.S. patent application Ser. No. 11/879,485 filed Jul. 16, 2007, entitled "Device with Needle Penetrable and Laser Resealable Portion and Related Method"; U.S. Pat. No. 6,929,040, entitled "Sterile Filling Machine Having Needle Filling within E-Beam Chamber"; U.S. Pat. No. 7,111,649, entitled "Sterile Filling Machine Having Needle Filling within E-Beam Chamber"; U.S. patent application Ser. No. 11/527,775 filed Sep. 25, 2006, entitled "Sterile Filling Machine Having Needle Filling within E-Beam Chamber"; U.S. Pat. No. 7,100,646, entitled "Sealed Containers and Methods of Making and Filling Same"; U.S. patent application Ser. No. 11/515,162 filed Sep. 1, 2006, entitled "Sealed Containers and Method of making and Filling Same; U.S. provisional patent application Ser. No. 60/518,685, filed Nov. 10, 2003, entitled "Needle Filling and Laser Sealing Station"; U.S. patent application Ser. No. 10/983,178 filed Nov. 5, 2004, entitled "Needle Filling and Laser Sealing Station; U.S. Pat. No. 7,096,896, entitled "Apparatus for Needle Filling and Laser Resealing"; U.S. patent application Ser. No. 11/510,961 filed Aug. 28, 2006; entitled "Apparatus for Needle Filling and Laser Resealing"; and U.S. patent application Ser. No. 11/901,467 filed Sep. 17, 2007 entitled "Apparatus for Needle Filling and Laser Resealing"; and U.S. patent application Ser. No. 11/339,966, filed Jan. 25, 2006, entitled "Container Closure with Overlying Needle Penetrable and Thermally Resealable Portion and Underlying Portion Compatible with Fat Containing Liquid Product, and Related Method."

The re-sealable stopper 72 is formed of a thermoplastic material defining a needle penetration region that is pierceable with a needle to form a needle aperture therethrough, and is heat re-sealable to hermetically seal the needle aperture by applying laser radiation at a predetermined wavelength and power thereto. The stopper 72 includes a thermoplastic body defining (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal the needle aperture formed in the needle penetration region thereof in a predetermined time period and substantially without burning the needle penetration region (i.e., without creating an irreversible change in molecular structure or chemical properties of the material). In some embodiments, the predetermined time period is approximately 2 seconds, is preferably less than or equal to about 1.5 seconds, and most preferably is less than or equal to about 1 second. In some of these embodiments, the predetermined wavelength of the laser radiation is about 980 nm, and the predetermined power of each laser is less than about 30 Watts, and preferably less than or equal to about 10 Watts, or within the range of about 8 to about 10 Watts. Also in some of these embodiments, the predetermined color of the material is gray, and the predetermined opacity is defined by a dark gray colorant (or pigment) added to the stopper material in an amount within the range of about 0.3% to about 0.6% by weight.

In addition to the thermoplastic materials described above, the thermoplastic material of the stopper 72 may be a blend of a first material that is preferably a styrene block copolymer, such as the materials sold under either the trademarks KRATON or DYNAFLEX, such as DYNAFLEX G2706-10000-00, or GLS 230-174 (Shore A=30), and a second material that is preferably an olefin, such as the materials sold under either the trademarks ENGAGE or EXACT, such as EXACT 8203, or GLS 230-176 (Shore A=42). In some embodiments, the first and second materials are blended within the range of about 50:50 by weight to preferably about 90:10 by weight, and most preferably about 90:5 by weight (i.e., first material:second material). The benefits of the preferred blend over the first material by itself are improved water or vapor barrier properties, and thus improved product shelf life; improved heat sealability; a reduced coefficient of friction; improved moldability or mold flow rates; and a reduction in hystereses losses.

Alternatively, the thermoplastic material of the re-sealable stoppers 72 may take the form of a styrene block copolymer sold by GLS Corporation of McHenry, Ill. under the designation LC 254-071. This type of styrene block copolymer compound exhibits approximately the following physical properties: (i) Shore A Hardness: about 28-29; (ii) Specific Gravity: about 0.89 g/cm$^3$; (iii) Color: approximately grey to dark grey; (iv) 300% Modulus, flow direction: about 181-211 psi; (v) Tensile Strength at Break, flow direction: about 429-498 psi; (vi) Elongation at Break, flow direction: about 675%-708%; and (vii) Tear Strength, flow direction: about 78-81 lbf/in.

In each of these embodiments, the predetermined color and opacity of the thermoplastic is defined by a grey colorant that is provided in an approximately 3% color concentrate (i.e., there is an approximately 33:1 ratio of the concentrate to the natural resin or TPE). The color concentrate contains about 88.83% carrier or base resin, the remainder is pigment, and the pigment is grey carbon black. Thus, the pigment is about 0.34% by weight of the resulting thermoplastic.

In addition, if desired, a lubricant of a type known to those of ordinary skill in the pertinent art may be added to or included within each of the above-mentioned thermoplastic compounds, in order to prevent or otherwise reduce the formation of particles upon penetrating the needle penetration region of the thermoplastic stopper with a needle or other filling member. In one embodiment of the present invention, the lubricant is a mineral oil that is added to the styrene block copolymer or other thermoplastic compound in an amount sufficient to prevent, or substantially prevent, the formation of particles upon penetrating same with the needle or other filling member. In another embodiment, the lubricant is a silicone, such as the liquid silicone sold by Dow Corning Corporation under the designation "360 Medical Fluid, 350 CST", or a silicone oil, that is added to the styrene block copolymer or other thermoplastic compound in an amount sufficient to prevent, or substantially prevent, the formation of particles upon penetrating same with the needle or other filling member. In one such embodiment, the silicone oil is included in an amount within the range of about 0.4% to about 1% by weight, and preferably within the range of about 0.4 to about 0.6% by weight, and most preferably within the range of about 0.51 or about 0.5% by weight.

Alternatively, the resealable stopper or like portions of the dispenser may be made with one or more of the materials disclosed in international PCT patent application no. PCT/EP2004/008703, (WO2005/014419 A1), filed Aug. 2, 2004, which claims priority to Great Britain patent application no. 031824.25, filed Aug. 4, 2003, each of which is hereby incorporated by reference as part of the present disclosure.

After needle filling the storage chamber 14 through, and laser resealing the stopper 72 of the plunger 40, a cap 84 is fixedly secured to the open end of the body 12 to prevent access to the interior of the body. The cap 84 includes one or more vent apertures (not shown) to prevent the formation of a vacuum between the plunger 40 and cap 84, and otherwise to allow the plunger 40 to freely travel through the body 12 upon dispensing the substance from the storage chamber 14.

Figure 7D:
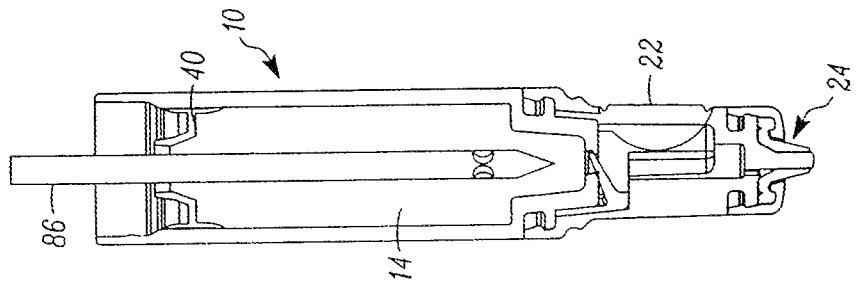
FIGS. 7A-7D are a series of somewhat schematic, cross-sectional views of the dispenser of FIG. 1 illustrating the filling of the storage chamber with a substance by penetrating the needle penetrable and laser resealable stopper of the piston forming the variable-volume storage chamber.
Figure 7C:
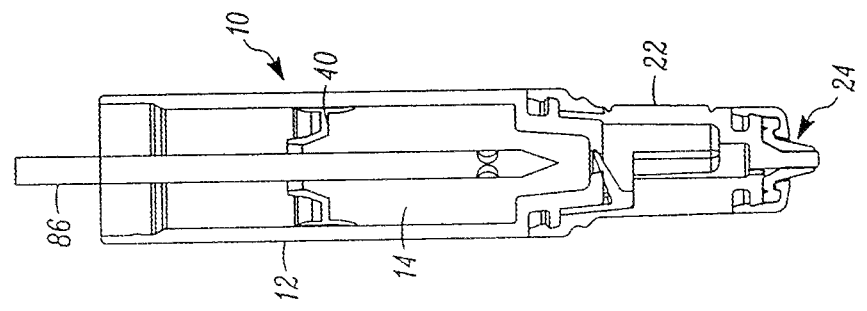
Figure 7B:
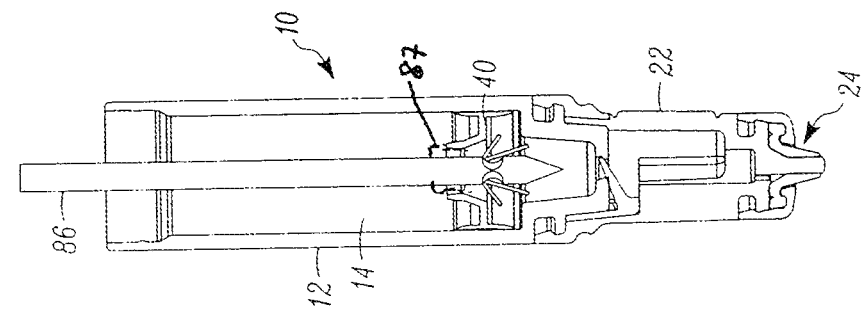
Figure 7A:
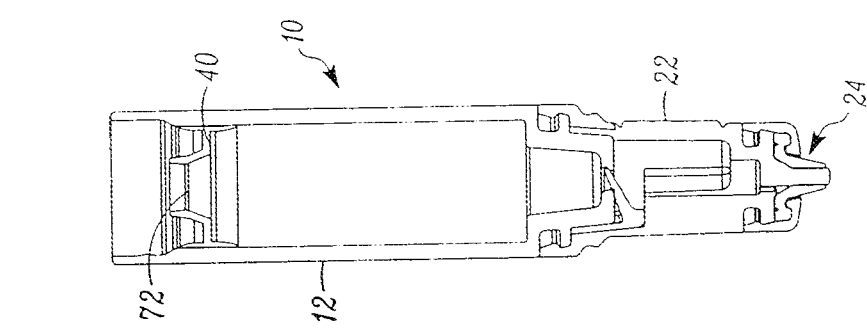

Turning to FIGS. 7A-7D, the dispenser 10 may be needle filled and laser resealed by first sterilizing the interior of the sealed empty dispenser, such as by applying radiation thereto, such as gamma or ebeam radiation. The sealed, empty, sterile dispenser 10 is then placed in a suitable fixture (e.g., a filling tray), or is already placed in such fixture during the sterilization step, so that the one-way valve 24 is facing down, and the needle penetrable and thermally resealable stopper 72 is facing up. Then, the stopper 72 is pierced with a non-coring needle or cannula 86 and the cannula and stopper are driven downwardly or inwardly from the "home" position, as shown in FIG. 7A, to the "start fill" position where the stopper and cannula are located at the inner end of the empty body 12, as shown in FIG. 7B. If desired, and as shown in broken lines in FIG. 7B, the needle 86 may include a collar 87 fixedly secured thereto and located adjacent to the pointed tip for engaging the exterior surface of the stopper 40 to facilitate driving the stopper from the home to the start fill position and otherwise prevent relative movement between the stopper and needle during this step. Then, as shown in FIG. 7B, the substance is injected through the needle 86 and into the chamber 14. As can be seen in FIGS. 7C and 7D, the substance fills the variable-volume storage chamber 14, and the stopper 40 moves upwardly toward the back end of the body until the variable-volume storage chamber is filled. In the embodiment employing the collar 87 (FIG. 7B), the needle is driven upwardly with the stopper from the start fill position back to the home position (as shown progressively in FIGS. 7B-7D) while the variable-volume storage chamber is filled due to the friction between the needle and stopper and the fluid pressure of the filled liquid against the stopper. Preferably, the retraction rate of the needle, and the fill rate of the fluid introduced into the chamber through the needle, are set so that the chamber is filled as the needle is withdrawn without causing a significant increase in fluid pressure, or a vacuum within the chamber. The needle 86 may include within it a vent conduit (not shown) allowing fluid, such as air, to be exhausted from the variable-volume storage chamber therethrough, or if desired, to allow fluid, such as nitrogen or other inert gas used as a purge, to be introduced into the variable-volume storage chamber therethrough. In addition, the vent conduit may be coupled in fluid communication with a vacuum source to pull a vacuum on the conduit, and in turn, draw fluid, such as air, out of the variable-volume storage chamber prior to and/or during the fill to prevent pressurization of any such air within the variable-volume storage chamber, and otherwise to remove air or other gases from the chamber. In one embodiment of the present invention, when the stopper 40 returns to the home position as shown in FIG. 7D, the filling is timed so that some of the filled liquid is drawn into the vent conduit (either by flowing into the conduit, or by being drawn into the vent conduit by the vacuum source) and/or into a container in fluid communication with the conduit or filling needle, in order to fully fill the variable-volume storage chamber and substantially prevent the formation of air pockets within the filled chamber. Any such significant air pockets can enter the dosage chamber of the pump, cause cavitation, and otherwise prevent dosing of filled liquid through the one-way valve. If desired, the stopper can be fixed in the home position throughout filling (i.e., the stopper is not moved during filling), and the needle can fill from a fixed position, or may be moved through the stopper during filling to perform a "bottom up" fill.

Figure 8C:
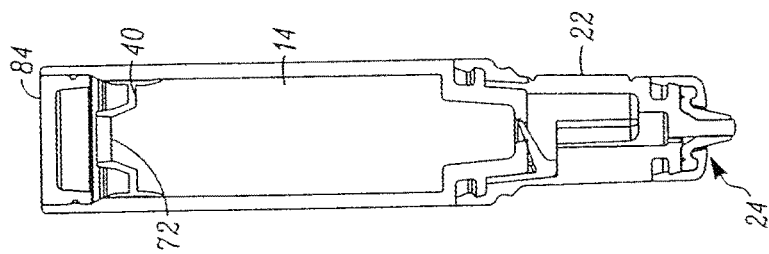
FIGS. 8A-8C are a series of somewhat schematic, cross-sectional views of the dispenser of FIG. 1 illustrating the withdrawal of the needle and laser resealing of the resulting needle hole formed in the stopper to hermetically seal the substance within the variable-volume storage chamber.
Figure 8B:
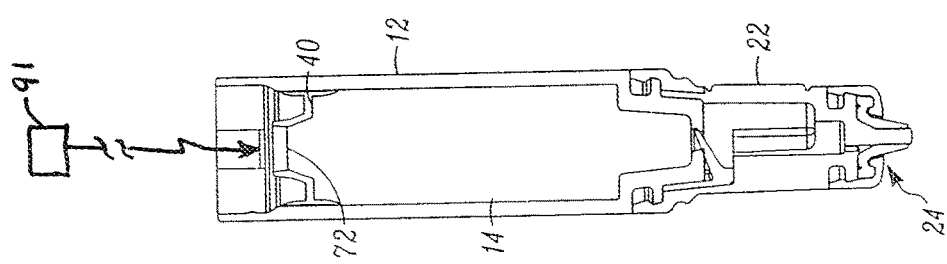
Figure 8A:
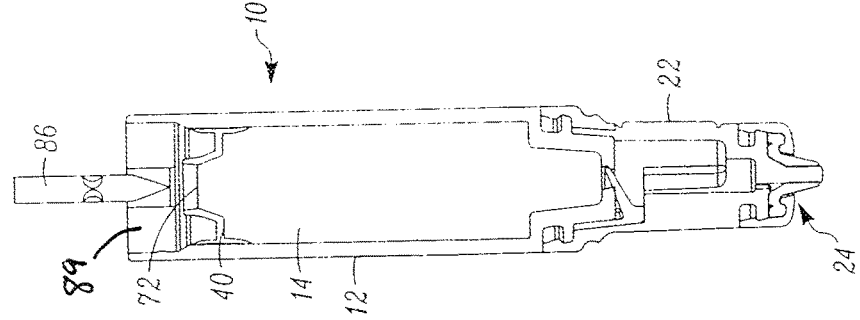

As shown in FIG. 8A, in the home position, a stop 89 of the filling apparatus is preferably received within the open end of the body 12 to engage the stopper 40 in the home position and thereby ensure proper positioning of the stopper and prevent the stopper from movement out of the body. As shown in FIG. 8A, in the home position, the needle 86 is withdrawn, and then as shown in FIG. 8B, a laser source 91 is activated to thermally reseal the resulting penetration aperture. Then, as shown in FIG. 8C, the cap 84 is installed to lock the stopper within the body. The cap 84 is snap fit into the back end of the body such that it cannot be removed from the body without breaking the cap to thereby provide a tamper-evident closure. If desired, the variable-volume storage chamber 14 may be over-filled by an amount approximately equal to the volume of the dosage chamber. Then, prior to installing the cap 84, the dispenser may be turned upwardly so that the one-way valve 24 is facing up, and the cap may be inserted into the back end of the body to, in turn, move the plunger 40 upwardly. The cap 84 may include a projection (not shown) on its interior side to effect this movement of the plunger upon attachment of the cap to the body. This, in turn, displaces a substantially predetermined amount of substance from the variable-volume storage chamber 14 into the dosage chamber 18 to fill the dosage chamber with substance and thereby prime the dispenser for the first dose. Orienting the dispenser in an upright position during this step will facilitate in allowing any air or other gas within the dosage chamber to be exhausted through the one-way valve 24 upon movement of the substance into the dosage chamber. If desired, the plunger 40 may be maintained in a fixed position on the body (i.e., at the back end 90 of the body) during needle filling rather than moving the plunger during filling.

Figures 10D, 10E, 10F:
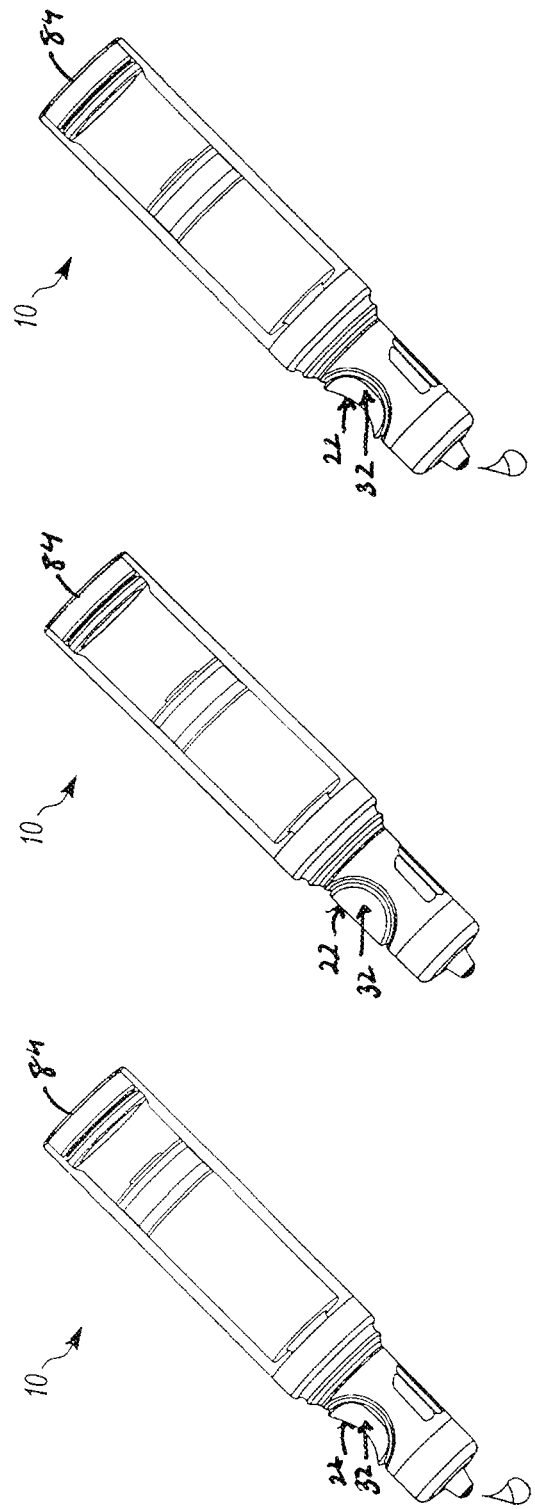

As shown in FIGS. 9 and 10A-10F, the dispenser 10 is actuated to dispense a drop of substance, such as an ophthalmic formulation, by engaging, such as with the index finger, the actuator 22 and depressing the actuator (FIG. 9). As indicated in FIG. 10B, depression of the actuator 22 pressurizes the substance within the dosage chamber 18 and, in turn, releases the dose in drop form through the one-way valve 24. Simultaneously, and as indicated in FIGS. 10B and 10C, the sliding piston 40 moves forward to compensate for the dispensed dose, and allows the next dose to flow into the dosage chamber. As shown in FIGS. 10D-10F and 11, as additional dosages are dispensed, the sliding stopper 40 progressively moves inwardly within the body 12 until the variable-volume storage chamber is emptied (FIG. 11)

If desired, and as shown in broken lines in FIG. 2, the dispenser 10 may further include a flexible membrane 88 coupled between the piston 40 and an end portion 90 of the body 12 opposite the dispensing portion, and forming a substantially fluid-tight seal between the annular piston and respective end portion of the body. If desired, the flexible membrane 88 may include a plurality of laminated layers to provide desired properties, such as desired barrier properties. Also in the illustrated embodiment, the flexible membrane 88 extends annularly about the piston 40 and about the respective end portion 90 of the body to effect a fluid-tight seal between the plunger and the ambient atmosphere. As shown typically in FIG. 9, the dispensing portion may include a plurality of axially elongated ribs 92 and axially elongated slots formed between the ribs, located on an opposite side of the dispensing portion 16 relative to the actuator 22 to provide a gripping surface. Also, the slots allow the wall thickness in this region of the dispensing portion to be reduced and thereby prevent the formation of sink holes in this relatively thick region of the part during molding.

Figure 12:
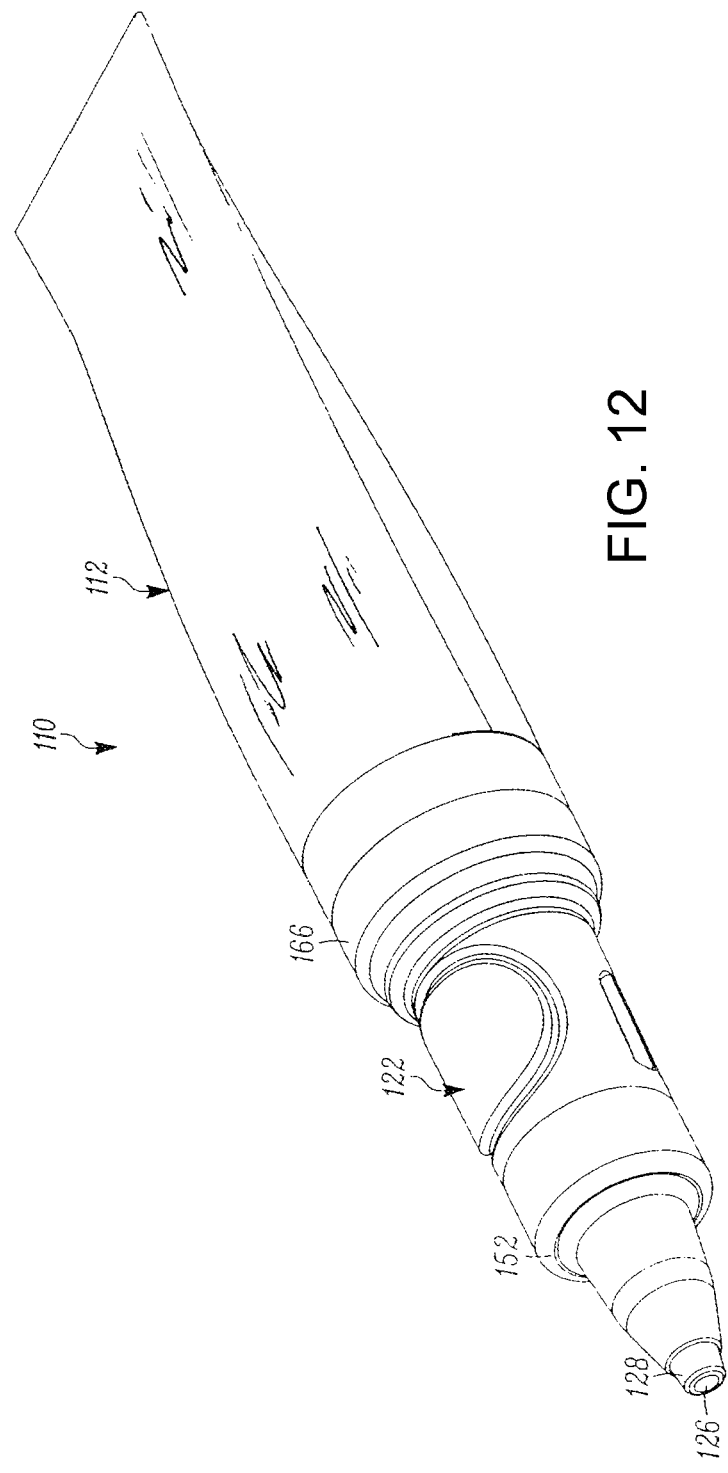
FIG. 12 is an upper perspective view of another embodiment of the present invention including a collapsible tube forming the variable-volume storage chamber, and a dispensing portion defining a more axially-elongated tip in comparison to the dispenser of FIG. 1 for dispensing, for example, creams or gels, onto an eye, nose, ear, etc.
Figure 13:
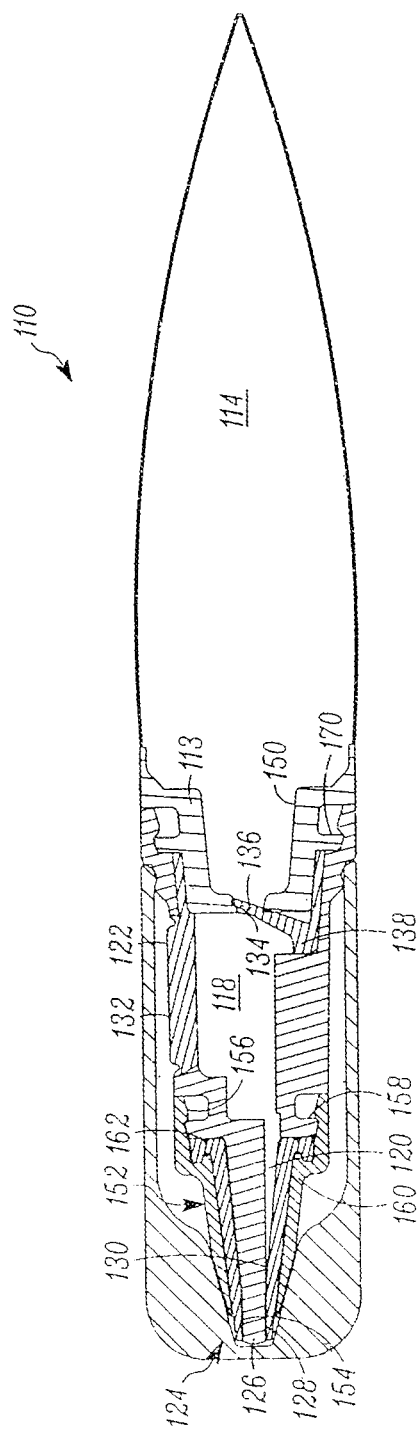
FIG. 13 is a cross-sectional view of the dispenser of FIG. 12.

Turning to FIGS. 12 and 13, another dispenser embodying the present invention is indicated generally by the reference numeral 110. The dispenser 110 is substantially similar to the dispenser 10 described above, and therefore like reference numerals preceded by the numeral "1" instead are used to indicate like elements. The primary difference of the dispenser 110 is that the body 112 is formed by a collapsible tube, and the dispensing tip defines a more axially-elongated or pointed configuration. In this embodiment, the body defines a tube head 113 that is preferably co-molded, such as by insert molding to the tube body 112. Also in this embodiment, each outlet aperture 120 is defined in part by an axially-elongated channel 121 that defines a progressively decreasing depth in the direction from the inner toward the outer end of the valve 124, and terminates at the seam 130 of the valve. The channel 121 may facilitate the flow of relatively viscous substances into and through the valve 124, such as creams and gels. In the illustrated embodiment, the dispenser 110 includes three outlet apertures 120 and corresponding channels 121 approximately equally spaced relative to each other about the valve seat 126. Also in the this embodiment, the securing member 152 extends axially along the valve cover 128; however, the distal portion of the valve cover extends outwardly of the securing member. In this embodiment, the collapsible tube 112 is filled through the open back end, and is then sealed (such as by ultrasonic sealing), in a manner known to those of ordinary skill in the pertinent art. To sterile fill the tube, and overpressure of sterile air or other gas may be provided during filling through the open back end of the tube.

The collapsible tube 112 of this embodiment may be constructed in accordance with the teachings of the following co-pending patent applications which are assigned to the Assignee of the present invention, and are hereby expressly incorporated by reference in their entireties as part of the present disclosure: U.S. Pat. No. 6,892,906, entitled "Container And Valve Assembly For Storing And Dispensing Substances, And Related Method", U.S. patent application Ser. No. 10/976,349 filed Oct. 28, 2004, entitled "Container And Valve Assembly For Storing And Dispensing Substances, And Related Method", U.S. Pat. No. D503,611, entitled "Container and Valve Assembly", U.S. Pat. No. D505,627, entitled "Tube and Valve Assembly", U.S. Pat. No. D515,436, entitled "Tube"; U.S. Pat. No. D538,158, entitled Tube and Valve Assembly; U.S. Patent application No. 29/273,719 filed Mar. 12, 2007, entitled Tube and Valve Assembly, U.S. Patent Application No. 60/528,429, filed Dec. 10, 2003, entitled "Valve Assembly And Tube Kit For Storing And Dispensing Substances, And Related Method," U.S. Patent Application No. 60/539,602, filed Jan. 27, 2004, entitled "Tubular Container And One-Way Valve Assembly For Storing And Dispensing Substances, And Related Method; U.S. patent application Ser. No. 11/008,887, filed Dec. 9, 2004, entitled "Container And One-Way Valve Assembly For Storing And Dispensing Substances, And Related Method".

As may be recognized by those of ordinary skill in the pertinent art based on the teachings herein, the variable-volume storage chamber may be formed in any of numerous different ways that are currently known, or that later become known, including, for example, by using a relatively flexible bladder mounted within a relatively rigid body. The variable-volume storage chambers formed with a flexible bladder may be constructed in accordance with the teachings of the following co-pending patent application which is assigned to the Assignee of the present invention, and is hereby expressly incorporated by reference in its entirety as part of the present disclosure: U.S. application Ser. No. 10/843,902, filed May 12, 2004, entitled "Dispenser and Apparatus and Method for Filling a Dispenser"; and U.S. application Ser. No. 11/349,873, filed Feb. 8, 2006, entitled "Dispenser and Apparatus and Method for Filling a Dispenser".

Figure 14:
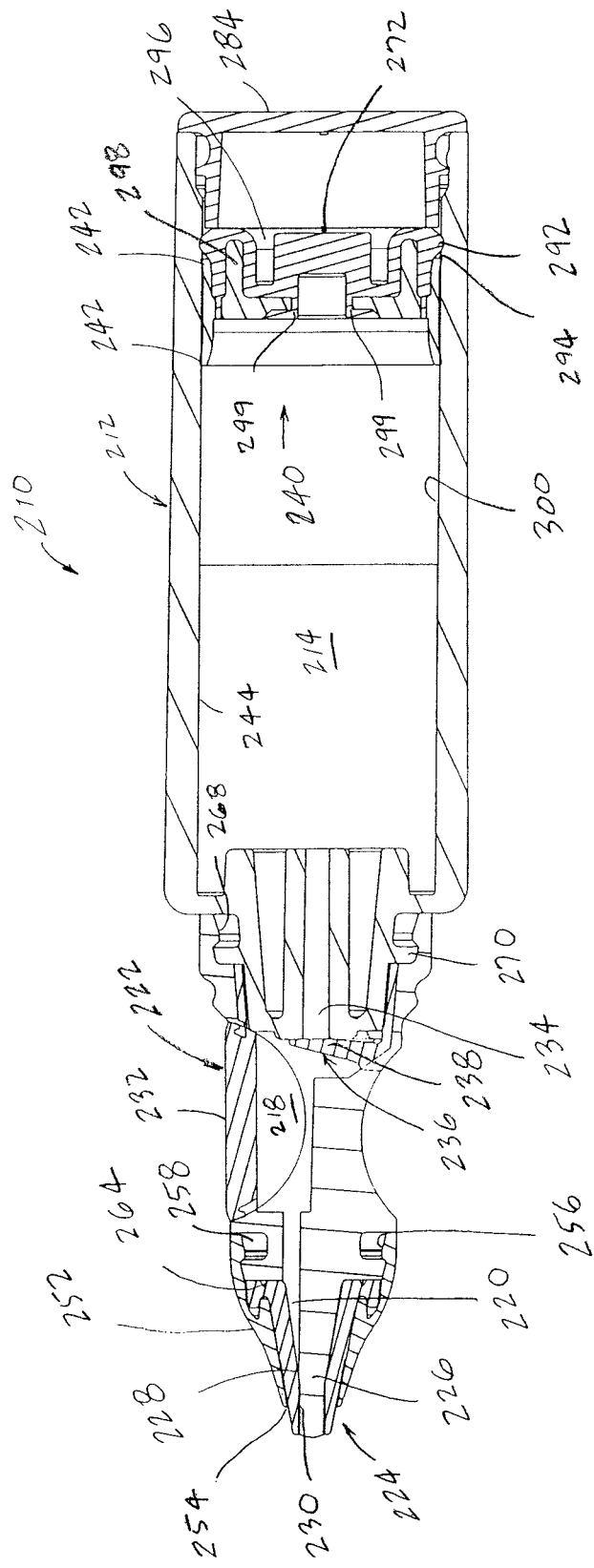
FIG. 14 is a cross-sectional view of another embodiment of a dispenser of the present invention wherein the penetrable and thermally resealable sliding stopper includes co-molded relatively rigid and relatively flexible annular sealing portions.

Turning to FIG. 14, another dispenser embodying the present invention is indicated generally by the reference numeral 210. The dispenser 210 is substantially similar to the dispensers 10 and 110 described above, and therefore like reference numerals preceded by the numeral "2", or preceded by the numeral "2" instead of the numeral "1", are used to indicate like elements. A primary difference of the dispenser 210 in comparison to the dispenser 10 above, is that the sliding stopper 240 includes in addition to the axially-spaced, relatively rigid annular sealing portions 242, a relatively flexible annular sealing portion 292. As can be seen, like the relatively rigid annular sealing portions 242, the relatively flexible annular sealing portion 292 forms an interference fit with the inner wall 244 of the body to form a hermetic seal therebetween. A first annular gap 294 is formed between the flexible sealing portion 292 and rigid sealing portion 242 to allow deformation of the flexible sealing portion therein during movement of the stopper. A second annular gap 296 is formed between the penetrable and thermally resealable stopper 272 and the flexible annular sealing portion 292. In the illustrated embodiment, a relative rigid support wall 298 is formed integral with the relatively rigid sealing portions 292 and extends axially adjacent to the second annular gap 296 to support and prevent creep of the flexible sealing portion 292. In the illustrated embodiment, the stopper 272 and flexible sealing portion 292 are co-molded with the relatively rigid portions 242, such as by over-molding the flexible portion to the rigid portion. The second annular gap 296 allows the molding gate to be located at approximately the center of the part, to relatively tightly control the tolerance of the outer diameter of the flexible sealing portion 292, and thus the consistency of the hermetic seal from one part to another, and to form a relatively thick stopper portion 272 to, in turn, form a relatively thick layer of homogenous material within the penetration depth of the laser and facilitate the formation of a hermetic laser reseal.

With respect to the relatively rigid sealing portions 242, the leading contact point (to the left in FIG. 14) is defined by the point of tangency between the radius of the relatively rigid sealing portion and the inner wall of the body, and the trailing contact point (to the right in FIG. 14) is defined by a point at the trailing edge of the part to minimize any frictional contribution and provide balance. The rigid portion of the stopper 240 defines plural flow paths 299 angularly spaced relative to each other about the central region of the stopper to allow any trapped air to flow out of the mold therethrough during molding, and thereby prevent the formation of air pockets within the flexible portions of the stopper. The rigid portion of the stopper may be made of any of numerous different materials that are currently known, or that later become known, such as a relatively rigid polyethylene. The flexible portion of the stopper, on the other hand, may be made of any of the materials described above for purposes of penetrating with a filling member and thermally resealing, or any of numerous other materials that are currently known, or that later become known for this purpose. The body 212 defines a first region 300 that tapers inwardly toward the inner end of the body to provide progressively more interference between the stopper and body as the stopper moves inwardly within the body. In the illustrated embodiment, the taper is about 0.5 degrees; however, other taper angles equally may be employed. The taper region 300 constitutes about one-half the length of the chamber (or the overall travel distance of the stopper). The other inner of the inner wall 244 defines a substantially zero taper.

As also may be recognized by those of ordinary skill in the pertinent art based on the teachings herein, the dispensing tip may take any of numerous different configurations to perform any of numerous different functions that are currently known or that later become known. For example, the contour of the dispensing tip may be shaped to comfortably contact a user's lips for purposes of applying a dose of liquid lipstick, other cosmetic, pharmaceutical, or other cosmetic substance thereto. As another example, the dispensing tip may take any of a variety of different forms designed to substantially conformably contact a user's eyelids, eyebrows, eyelashes, cheeks, toenails, fingernails, etc., or to deliver fluids or other substances in any desired manner. The dispensing tip may be shaped to effectively deliver ophthalmic products, such as eye drops, in a manner that releases the drop at a substantially predetermined location on the tip, and that allows substantially the entire dosage to be released, to thereby facilitate a substantially consistent drop size or volume from one dosage to the next. Alternatively, the dispensing tip may be configured to deliver substances to any desired body surface or cavity, including, for example, dispensing tips that are configured to deliver dosages to the nasal, ear (i.e., otic delivery), vaginal, penis and/or anal cavities, dispensing tips configured to deliver dosages to the scalp, or dispensing tips configured to deliver dosages to fingernails and/or toe nails, including dispensing tips configured to deliver substances underneath the nails, on the tops of the nails, or to the cuticles of the nails. In another exemplary embodiment, the dispenser is configured to dispense food or beverage products, including, for example, flavorings for coffee or other beverages. In some such embodiments, the dispensing tip may be shaped to facilitate insertion into, or engagement by a user's mouth for dispensing the product into the mouth. In other such embodiments, the dispensing tip may be shaped to facilitate dispensing the respective product into a cup or other beverage or food product container. Accordingly, as may be recognized by those of ordinary skill in the pertinent art based on the teachings herein, the specific shape and/or configuration of the dispensing tip and/or of an applicator surface of the dispensing tip, may take any of numerous different shapes or configurations that are currently known, or that later become known for performing any of numerous different functions, and/or to address the requirements of any of numerous different applications of the dispensers for delivering any of numerous different substances that are currently known, or that later become known.

As may be recognized by those of ordinary skill in the pertinent art based on the teachings herein, numerous other changes and modifications may be made to the above-described and other embodiments of the present invention without departing from the scope of the invention as defined in the claims. For example, the components of the dispensers may be made of any of numerous different materials that are currently known, or that later become known for performing the function(s) of each such component. Similarly, the components of the dispensers may take any of numerous different shapes and/or configurations. Also, the dispensers may be used to dispense any of numerous different types of fluids or other substances for any of numerous different applications, including, for example, cosmetic, dermatological, ophthalmic or other pharmaceutical, cosmeceutical, OTC food and/or beverage applications. In addition, the characteristics of the dispensers may be adjusted, including for example the shape and/or configuration of the dispensing tip, the volume of the dosages, and/or the valve opening pressure, to meet the requirements of any of numerous different applications and/or products to be dispensed, including without limitation products that are delivered topically, such as to the skin or to mucous membranes, products that are delivered to the ear (i.e., otic delivery), to the penis, nasally, vaginally, anally or orally. In addition, the dispensers may be actuated other than manually. For example, the dispenser may be mounted in a dispensing machine, and automatically actuated, such as by a solenoid, solenoid-driven actuator, or actuated by depressing a manually-engageable button or other actuator that, in turn, depresses an elastic or other actuator to dispense doses of substance, such as a flavoring, into a beverage container. Further, the filling machines and processes used to fill the dispensers of the present invention may take any of numerous different configurations that are currently known, or that later become known for filling the dispensers. For example, the filling machines may have any of numerous different mechanisms for sterilizing, feeding, evacuating and/or filling the dispensers. If desired, the surface contour of the valve seat may be adjusted to facilitate directing the valve-flow through a predetermined dispensing location at the valve tip. In addition, rather than use the needle penetrable and resealable actuator, plunger, or other like stopper, the dispenser may employ a filling valve as disclosed in the following patent application that is assigned to the Assignee of the present invention, and is hereby incorporated by reference in its entirety as part of the present disclosure: U.S. application Ser. No. 10/843,902, filed May 12, 2004, titled "Dispenser and Apparatus and Method for Filling a Dispenser"; and U.S. application Ser. No. 11/349,873, filed Feb. 8, 2006, entitled "Dispenser and Apparatus and Method for Filling a Dispenser". In such alternative embodiments, the filling valve may extend through the body or otherwise may be coupled in fluid communication with the storage chamber to evacuate and/or fill the storage chamber. Alternatively, the dispenser may include one valve for evacuating the interior of the dispenser and another valve for filling the storage chamber of the dispenser. Still further, the valves each may take a configuration that is different than that disclosed herein. Accordingly, this detailed description of currently preferred embodiments is to be taken in an illustrative, as opposed to a limiting sense.

What is claimed is:

1. A method comprising the following steps:
   filling a sealed, empty device including a body, a slidable stopper slidingly received within the body of the sealed, empty device and defining a variable-volume storage chamber therein, and a one-way valve, the filling step including:
   slidably receiving the stopper within the body;
   after the receiving step, fixing the slidable stopper relative to the body with the stopper located in a first position within the body such that the slidable stopper cannot move from the first position;
   engaging an exterior back surface of the slidable stopper with a collar of a filling apparatus that includes: (i) said collar and (ii) a filling member;
   penetrating the stopper with the filling member with the stopper fixed relative to the body and located in the first position such that the slidable stopper does not move from the first position during penetration;
   introducing a fluid into the variable-volume storage chamber through the filling member;
   withdrawing the filling member; and
   sealing an aperture in the slidable stopper to seal the variable-volume storage chamber.

2. A method as defined in claim 1, further comprising the step of sterilizing the sealed empty device prior to the filling step.

3. A method as defined in claim 1, further comprising the step of drawing a vacuum through one or more of the filling member or a filling aperture during the filling step.

4. A method as defined in claim 3, further comprising drawing with the vacuum fluid out of the variable-volume storage chamber and into one or more of a filling member conduit or a collection container during the filling step, to thereby leave substantially zero air within the chamber after the withdrawing step.

5. A method as defined in claim 1, further comprising the step of providing an overpressure of sterile air over one or more of the filling member or the device during the filling step.

6. A method as defined in claim 1, wherein the sealing step comprises applying radiation or energy to the slidable stopper.

7. A method as defined in claim 6, wherein the radiation or energy comprises one or more of laser radiation or thermal energy.

8. A method as defined in claim 1, wherein the device further includes a dosage chamber connectable in fluid communication between the one-way valve and the variable-volume storage chamber, and an actuator movable between a non-actuated position and an actuated position for compressing a dose of fluid within the dosage chamber and dispensing the dose through the one-way valve.

9. A method as defined in claim 1, further comprising the step of moving the slidable stopper further within the body from the first position after the filling step and prior to dispensing fluid from the device.

10. A method comprising the following steps:
    filling a sealed, empty device including a body, a slidable stopper slidingly received within the body and defining a variable-volume storage chamber therein, and a one-way valve, the filling step including the following steps (a) through (e) performed in sequence:
    (a) penetrating the slidable stopper with a filling member and the stopper located in a first position within the body;
    (b) moving the slidable stopper to a second position within the body during or after penetrating the slidable stopper with the filling member;
    (c) introducing a fluid into the variable-volume storage chamber through the filling member after said moving step;
    (d) withdrawing the filling member; and
    (e) sealing an aperture in the slidable stopper to seal the variable-volume storage chamber.

11. A method as defined in claim 10, further comprising moving the slidable stopper from the first position to further within the body after the filling step and prior to dispensing fluid from the device.

12. A method as defined in claim 10, further comprising the step of moving the filling member and the slidable stopper from the second position back to the first position while introducing the fluid into the variable-volume storage chamber.

13. A method as defined in claim 10, further comprising the step of sterilizing the sealed empty device prior to the filling step.

14. A method as defined in claim 10, further comprising the step of drawing a vacuum through one or more of the filling member or a filling aperture during the filling step.

15. A method as defined in claim 14, further comprising drawing with the vacuum fluid out of the variable-volume storage chamber and into one or more of a filling member conduit or a collection container during the filling step, to thereby leave substantially zero air within the chamber after the withdrawing step.

16. A method as defined in claim 10, further comprising the step of providing an overpressure of sterile air over one or more of the filling member or the device during the filling step.

17. A method as defined in claim 10, wherein the sealing step comprises applying radiation or energy to the slidable stopper.

18. A method as defined in claim 17, wherein the radiation or energy comprises one or more of laser radiation or thermal energy.

19. A method as defined in claim 10, wherein the device further includes a dosage chamber connectable in fluid communication between the one-way valve and the variable-volume storage chamber, and an actuator movable between a non-actuated position and an actuated position for compressing a dose of fluid within the dosage chamber and dispensing the dose through the one-way valve.

20. A method comprising:
    filling a sealed, empty device including a body, a slidable stopper slidingly received within the body and defining a variable-volume storage chamber therein, and a one-way valve, the filling step including the following steps
    (a) through (e) performed in sequence:
    (a) penetrating the slidable stopper with a filling member and the stopper located in a first position within the body;
    (b) moving the slidable stopper to a second position within the body during or after penetrating the slidable stopper with the filling member, wherein the moving step further comprises moving the filling member to the second position within the body during or after penetrating the slidable stopper with the filling member;
    (c) introducing a fluid into the variable-volume storage chamber through the filling member after said moving step, wherein, during the introducing step, the slidable stopper moves toward the first position and the filling member remains substantially in the second position;
    (d) withdrawing the filling member; and
    (e) sealing an aperture in the slidable stopper to seal the variable-volume storage chamber.

* * * * *